United States Patent [19]

Magee et al.

[11] Patent Number: 4,548,929
[45] Date of Patent: Oct. 22, 1985

[54] INSECTICIDAL AND NEMATOCIDAL HETEROBICYCLIC HYDROXIMINATES, THIOHYDROXIMIDATES, AND CARBAMATE ESTERS, COMPOSITION, AND METHOD OF USE THEREOF

[75] Inventors: Thomas A. Magee, Mentor; Robert D. Battershell, Painesville; Lawrence E. Limpel, Euclid, all of Ohio; Andrew W. Ho, Pinole, Calif.; Arthur W. Friedman, Beachwood, Ohio; H. Glenn Corkins, Ewing, N.J.; William W. Brand, Painesville, Ohio; Russell Buchman, Madison, Ohio; Louis Storace, Mentor-on-Lake, Ohio; Edmond R. Osgood, Mentor, Ohio

[73] Assignee: SDS Biotech Corporation, Painesville, Ohio

[21] Appl. No.: 486,211

[22] Filed: Apr. 18, 1983

Related U.S. Application Data

[60] Division of Ser. No. 317,516, Nov. 2, 1981, Pat. No. 4,424,213, which is a continuation-in-part of Ser. No. 205,436, Nov. 10, 1980, abandoned.

[51] Int. Cl.$^4$ .................. A01N 43/10; A01N 43/12; A01N 43/18; A01N 43/40; C07D 311/02; C07D 313/08; C07D 407/12; C07D 417/12

[52] U.S. Cl. .................................. 514/85; 514/89; 514/90; 514/99; 514/222; 514/227; 514/255; 514/277; 514/320; 514/359; 514/450; 514/456; 514/256; 544/57; 544/58.1; 544/58.2; 544/58.7; 544/60; 544/61; 544/150; 544/151; 544/243; 544/298; 544/316; 544/319; 544/333; 544/335; 548/525; 546/22; 549/214; 549/220; 546/24; 549/354; 549/355; 546/196; 549/386; 549/397; 546/269; 548/406; 548/414

[58] Field of Search ............ 424/200, 203, 246, 248.4, 424/250, 251, 263, 267, 274, 278, 283; 544/57, 58.1, 58.2, 58.7, 60, 61, 150, 151, 243, 298, 316, 319, 333, 335; 546/22, 24, 196, 269; 548/406, 414, 525; 549/214, 220, 354, 355, 386, 397

[56] References Cited

U.S. PATENT DOCUMENTS 3,538,117 11/1970 Tobey et al. .................... 549/397

OTHER PUBLICATIONS

Moriconi et al., J. Org. Chem., vol. 41, No. 22, 1976, pp. 3583-3586.

Primary Examiner—Henry R. Jiles
Assistant Examiner—J. G. Mullins
Attorney, Agent, or Firm—John P. Hazzard

[57] ABSTRACT

Novel heterobicyclic compounds of Formula I, processes for preparing same and pesticidal compositions and methods are described.

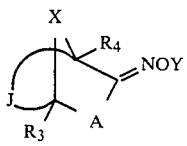

4 Claims, No Drawings

INSECTICIDAL AND NEMATOCIDAL HETEROBICYCLIC HYDROXIMINATES, THIOHYDROXIMIDATES, AND CARBAMATE ESTERS, COMPOSITION, AND METHOD OF USE THEREOF

CROSS REFERENCE TO RELATED APPLICATION

This is a division, of application Ser. No. 317,516, filed Nov. 2, 1981, now U.S. Pat. No. 4,424,213 which is a continuation-in-part of pending U.S. patent application having Ser. No. 205,436 now abandoned.

BACKGROUND OF THE INVENTION

The present invention relates generally to biologically active hydroximidates, thiolhydroximidates, amidoximes and, more particularly, to novel pesticidally active carbamate and sulfenylated carbamate derivatives thereof.

Carbamate derivatives of hydroximidates and thiolhydroximidates have heretofore been previously described. For example, U.S. Pat. No. 3,576,834 discloses acyclic compounds of the structure $$R_1-C(QR_4)=NOCN(R_2)(R_3) \text{ with } C=O$$

wherein Q is sulfur or oxygen and the insecticidal and acaricidal activity thereof.

Similarly, carbamates of monocyclic thiolhydroximidates of the structure

[structure with $R_1, R_2, R_3, R_4, R_5, R_6, R_7, R_8, R_9, R_{10}$ and $(C)_n$]

are disclosed in U.S. Pat. No. 3,317,562 as insecticides.

Carbamate derivatives of bicyclic oximes have been previously reported. U.S. Pat. No. 3,231,599 discloses compounds of the structure (XXI) and (XXII)

as insecticidally active compounds.

Further, Belgian Pat. No. 766109 quinuclidine oxime carbamates of the structure (XXIII)

also with reported insecticidal activity.

U.S. Pat. Nos. 3,317,562 and 3,574,233 further disclose thiabicycloalkanes and -alkenes of the formulas The patentees indicate that compounds of the above formulas possess insecticidal, fungicidal, nematicidal, antibacterial and herbicidal activity. It will be appreciated that the foregoing thiabicycloalkanes and alkenes are not carbamates.

U.S. Pat. No. 4,219,658 discloses lactones and thiolactones of the formulas as intermediates in the preparation of hydrocarbylthiomethyl-2,2-dimethylcyclopropane carboxylic acids useful as pesticides.

It has now been surprisingly found, in accordance with the present invention, that substituted heterobicyclic compounds of the formula (I)

(I)

as defined hereinafter possess a broad range of useful biological properties, as well as a high degree of activity as arthropodicides, i.e., insecticides, acaricides, aphicides, etc., as well as nematicides.

As detailed hereinbelow, the compounds of the above formula (I) are chemically and biologically distinguishable from the acyclic and monocyclic hydroximidates and thiolhydroximidates, bicyclic oximes and thiabicyclo-alkanes and -alkenes described above in reference to heretofore suggested compounds by reason of the mode of action, type of action and level of action demonstrated for the compounds of the present invention, as well as the fact that the compounds of the present invention are not obtainable by previously suggested synthesis methods employed to prepare the prior art compounds which appear to be structurally similar.

Certain of the compounds of the present invention are derived from Diels-Alder adducts of thiocarbonyl compounds with cyclic dienes. the ability of carbon-sulfur double bonds to serve as dienophiles in the Diels-Alder reaction was first reported in 1965 by Middleton [*J. Org. Chem.* 30, 1390 (1965)] who described the reactions of perfluorinated thioketones, thiophosgene and thiocarbonyl fluoride with several dienes, including cyclopentadiene, e.g.,

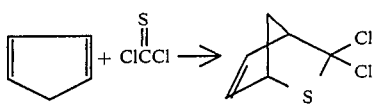

Since that time, many other examples of such reactions have been reported, including in addition to the above dienophiles such thiocarbonyl compounds as NCC(=S)SCH$_3$ [*Can. J. Chem.* 49, 3755 (1971)], NCC(=S)NR$_1$R$_2$ [*Tetrahedron Letters*, 2139 (1977)]RSO$_2$C(=S)SR' [*Tetrahedron* 30, 2735 (1974)], and

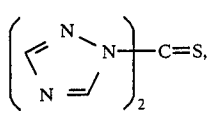

A limited number of reports have appeared on further reactions of the initial Diels-Alder adducts. Johnson et al. [*J. Org. Chem.* 34, 860 (1969)]describe oxygenation of the sulfur, followed by epoxidation of the double bond as depicted below:

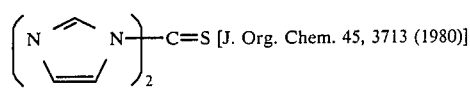

The authors indicate that one chlorine can be reduced from the dichloro sulfone by treatment with divalent chromium:

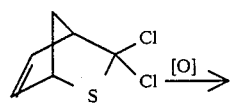

Reduction with lithium aluminum hydride yields the bicyclic thioalkene:

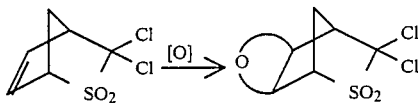

In 1973, Reich et al. [*J. Org. Chem.* 38, 2637 (1973)] reported the reaction of thiophosgene with cyclohexadienes, to yield 3,3-dichloro-2-thiabicyclo[2.2.2]oct-5-enes, as well as the hydrolysis of these Diels-alder adducts to the corresponding thiolactones.

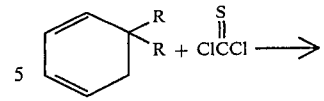

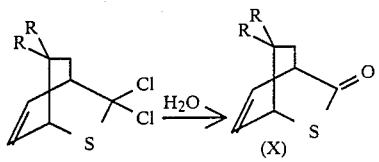

Benassi et al. [*Synthesis* 735 (1974)] describe a similar hydrolysis in the [2.2.1] system during reduction using an aqueous workup procedure:

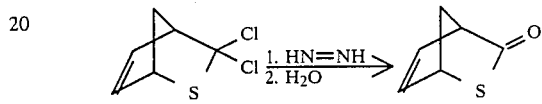

Raasch [*J. Org. Chem.* 40, 161 (1975)] reports on the addition of halogen or sulfenyl halides to the carbon-carbon double bond of the 2-thiabicyclo[2.2.1]hept-5-enes with rearrangement to yield the 6,7-disubstituted thiabicyclo[2.2.1]-heptanes, e.g.,

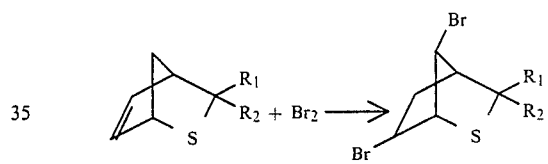

In 1976, Allgeier et al. [*Tetrahedron Letters*, 215 (1976)] also described the reaction of thiophosgene with anthracene to give the Diels-Alder adduct which is subsequently hydrolyzed to the thiolactone. Hong [*Dissertation Abstracts International* 40, 5672-B (1980)] states that solvolysis with methanol of the Diels-Alder adduct from thiophosgene and cyclopentadiene results in ring opening to yield (XIV) in almost quantitative yield.

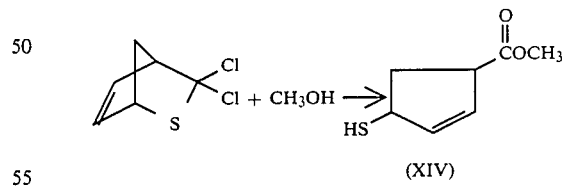

(XIV)

For purposes of indexing, *Chemical Abstracts* classifies compounds of type X above as 2-thiabicyclo[2.2.-2]oct-5-en-3-ones. In referring to these compounds, it is important to distinguish nomenclature used for indexing convenience from nomenclature signifying chemical type. Thus, *Chemical Abstracts* refers to both compounds XV and XVI (shown below) as thiabicycloalkanones. Chemically, however, compound XV is a thiolactone, i.e., a cyclic thiolester; whereas compound XVI [*J. Org. Chem.* 43, 4013 (1978)] is a true ketone and specifically a β-thioketone.

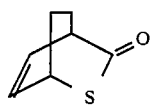 (XV)

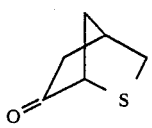 (XVI)

Esters and ketones are distinct chemical classes with many distinctly different properties. One of these distinctions is their reactivity with hydroxylamine. Ketones are known to react readily with hydroxylamine to form oximes:

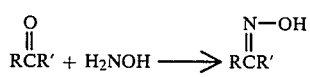

Esters or thiolesters (and their cyclic counterparts, lactones and thiolactones) do not react with hydroxylamine to yield the analogous hydroximidates or thiolhydroximidates.

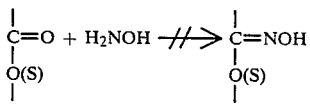

Instead they react with cleavage of the carbon-oxygen or carbon-sulfur single bond to yield as displacement products, the hydroxamic acid or, in the case of the lactones and thiolactones, a lactam (*Advanced Organic Chemistry*, Second Edition, Jerry March, McGraw-Hill Book Company, New York, 1977, p. 386, 388).

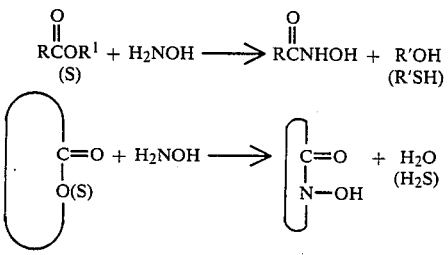

An example of the failure of thiolactones to react with hydroxylamine to yield thiolhydroximidates is reported by Bruice and Fedor [*J. Am. Chem. Soc.* 86, 4886 (1964)]. The authors confirm that thiolactones, e.g., thiolbutyrolactone, undergo hydroxylaminolysis in a manner analogous to their thiolester acyclic counterparts.

The hydroximidates and thiolhydroximidates, i.e.,

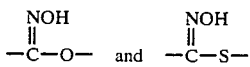

have been reported in the literature. At least four methods of preparation have been described. U.S. Pat. No. 3,576,834 (and the references therein) describes two of these: (1) the reaction of an iminoether hydrochloride with hydroxylamine and (2) chlorination of an aldoxime to form a hydroxamoyl chloride followed by reaction of the latter with a salt of a mercaptan:

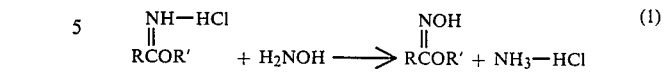 (1)

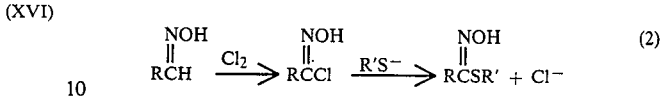 (2)

U.S. Pat. No. 3,787,470 reports the formation of thiolhydroxamate esters from nitroalkanes and alkyl mercaptans:

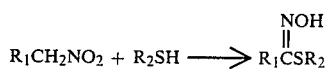

Faust et al. [*Journal fuer Praktische Chemie*, Leipzig, 311(1), 61, (1969)] describe the conversion of a thiopyranthione to a cyclic thiolhydroximidate.

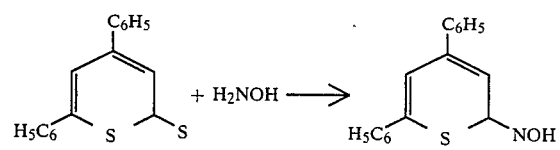

It will be seen from the foregoing that applicants have discovered that the Diels-Alder adducts of certain thiocarbonyl compounds with cyclic dienes are converted easily and in high yield to bicyclic thiolhydroximidates which not only possess significant biological activity but which are valuable as intermediates in the synthesis of carbamate and sulfenylated carbamate final products. Moreover, the outstanding arthropodicidal and nematicidal activity exhibited by these compounds is entirely unexpected in light of the prior art set forth hereinabove which relates to the ease of hydrolysis of the thiophosgene adducts, along with the reported inability of the thiolactones thus formed to react with hydroxylamine to yield compounds of the subject invention.

In addition to the above observations relative to the absence of prior art synthesis methods which would allow one to predictably obtain the compounds of the present invention by analogy, it is likewise important to note the material differences in biological activity observed with the compounds of the present invention compared to that of the seemingly related prior art compounds described hereinabove. In making such comparisons, it is again important to distinguish between nomenclature used for indexing convenience and nomenclature signifying actual chemical type. For example, for indexing purposes, *Chemical Abstracts* would describe the compounds of the present invention, as well as those of formulas (XXI)-(XXIII) as carbamates of bicycloalkanone oximes. However, in reality, the compounds of formulas (XXI)-(XXIII) are derivatives of true oximes; whereas, the compounds of the present invention are derivatives of hydroximidates or thiolhydroximidates. The significance of the foregoing distinction is readily apparent when one considers the work of Huhtanen and Dorough [*Pesticide Biochemistry and Physiology* 6, 571 (1976)] who have shown that the chemical difference between the ketoxime derivative XXIV and the thiolhydroximidate derivative XXV

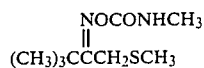 (XXIV)

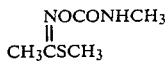 (XXV)

results in surprisingly marked differences in their biological activity. Although both (XXIV) and (XXV) are insecticides, their spectrum of activity, persistence, use pattern and method of application are totally different. It is evident that these documented differences result from the difference in chemical structure between a true ketoxime and a thiolhydroximidate. It will also be appreciated that a similar distinction between the compounds of the present invention and compounds of formulas (XXI)–(XXIII) prevails.

SUMMARY OF THE INVENTION

It is, therefore, a primary object of the present invention to afford novel substituted heterobicyclic compounds which possess outstanding pesticidal activity.

It is a further object of the present invention to provide novel processes for preparing heterobicyclic hydroximidate, thiolhydroximidate and carbamate compounds.

A still further object of the present invention is to provide arthropodicidally and nematicidally active compositions and methods for controlling undesired pests by the application of the novel compounds and pesticidal compositions of the invention to their habitat, food supply or breeding sites.

Still another object of the present invention is to provide novel heterobicyclic hydroximidates, thiolhydroximidates, and amidoximes which display arthropodicidal, nematicidal, bactericidal, fungicidal, plant growth regulant and anthelmintic activities, as well as being useful as novel intermediates for the preparation of carbamate and sulfenylated carbamate product derivatives.

These and other similar objects, advantages and features are accomplished according to the products, compositions and methods of the invention comprised of novel substituted heterobicyclic compounds, compositions derived therefrom and pesticidal methods employing same.

DESCRIPTION OF THE PREFERRED EMBODIMENTS

As stated previously, the present invention relates to substituted heterobicyclic compounds of the general formula (I)

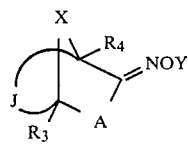 (I)

wherein
A represents S, O, S(O)$_m$ where m is 1 or 2 or NR$_5$ where R$_5$ is hydrogen, alkyl, aryl or cyano;
J represents the group

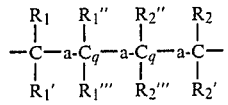

where q, independently, is 0 or 1, a, independently, is a single or double bond and R$_1$, R$_1'$, R$_1''$, R$_1'''$, R$_2$, R$_2'$, R$_2''$ and R$_2'''$ are defined below;
X is O, S, NR$_6$,

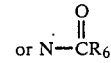

where R$_6$ is hydrogen or alkyl, or wherein X represents a bridge member selected from

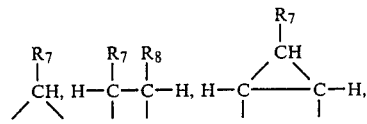

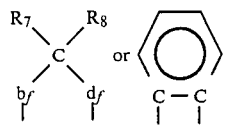

where R$_7$ and R$_8$ independently represent hydrogen, halogen, cyano, alkyl, alkoxy, alkoxycarbonyl or alkylthio and b-d independently represent carbon or oxygen and f is 0 or 1;
R$_1$-R$_1'''$, inclusive, R$_2$-R$_2'''$, inclusive, R$_3$ and R$_4$ independently represent hydrogen, halogen, hydroxy, cyano, alkyl, alkoxy, haloalkyl, alkylcarboxy, arylcarboxy, alkylaminocarboxy, carbamonyl, alkylcarbamoyl, dialkylcarbamoyl, alkylthio, alkylsulfinyl, alkylsulfonyl, alkylamino, dialkylamino, alkoxycarbonyl, trifluoromethyl, pyrrolidyl, phenyl, nitro, thiocyano, thiocarbamyl, alkylthiocarbamyl, dialkylthiocarbamyl, arylthiocarbamyl or the group

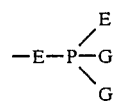

where E is O or S and G represents alkyl, alkoxy, alkylthio, amino, alkylamino or dialkylamino; or when a is a single bond and at least two of R$_1'$, R$_1'''$, R$_2'$ or R$_2'''$ are hydrogen on adjacent C atoms, then R$_1$, R$_1''$, R$_2$ or R$_2''$ on the same adjacent C atoms together may represent

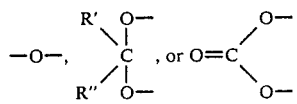

where R' and R'' represent hydrogen or alkyl; or any of R$_1$ and R$_1'$, R$_1''$ and R$_1'''$, R$_2''$ and R$_2'''$ or R$_2$ and R$_2'$ represent =O; or when q, independently, is 0 or 1 and a, independently, is a double bond, R$_1'$ R$_1'''$, R$_2'''$ or R$_2'$ are absent;
Y represents hydrogen or

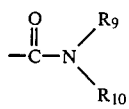 (1)

where $R_9$–$R_{10}$ independently represent hydrogen, alkyl, hydroxyalkyl, alkynyl, aralkyl, alkoxyalkyl or polyoxyalkylene; or

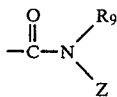 (2)

where $R_9$ is the same as defined before and Z represents

 (a)

where n is 0, 1 or 2 and $R_{11}$ is pyridyl, pyrimidyl, phenyl or phenyl substituted with at least one member selected from hydroxy, alkyl, alkoxy, halogen nitro, trifluoromethyl or cyano;

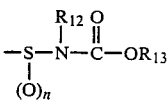 (b)

where n is 0, 1 or 2, and $R_{12}$ is alkyl, alkoxyalkyl, or

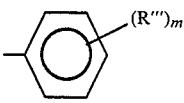

where m is 0, 1, 2 or 3 and R''' is hydrogen, halogen, cyano, nitro, alkyl, alkoxy, alkylthio, alkylsulfonyl or phenyloxy and $R_{13}$ is alkyl, alkoxyalkyl, naphthyl, alkylthioalkyl

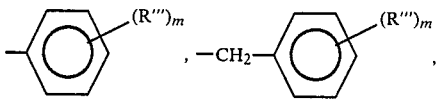

where (R''') is as defined before,

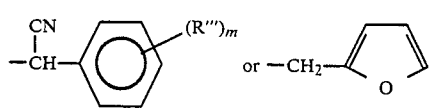

or Q where Q-OY represents formula (I) as defined herein;

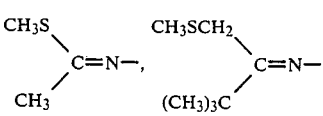 (c)

where $R_{12}$–$R_{13}$ are as defined before;

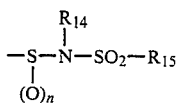 (d)

where n is 0, 1 or 2, $R_{14}$ is phenyl, alkyl, alkoxyalkyl, acyl, alkoxycarbonylalkyl, alkylthioalkyl, carboxyalkyl and $R_{15}$ is alkyl,

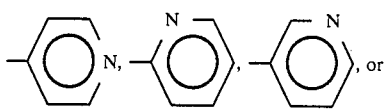

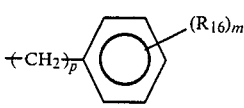

where m is 0–5, p is 0–5 and $R_{16}$ is halogen, alkyl, trifluoromethyl, nitro or alkoxy;

(e) —S—N$R_{17}R_{18}$ where $R_{17}$–$R_{18}$ are alkyl, aryl or together with the nitrogen atom represent

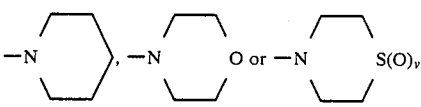

where v is 0, 1 or 2 or

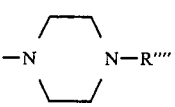

where R'''' is alkyl;

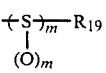 (f)

where n is 0, 1 or 2, m is 1 or 2 and $R_{19}$ is alkyl, cycloalkyl, haloalkyl, cyanoalkyl, alkoxycarbonyl, (alkylthio)carbonyl, alkoxy(thiocarbonyl), alkylthio(thiocarbonyl), aryl or substituted aryl with at least one substituent selected from halogen, cyano, nitro, alkyl, alkoxy, alkylthio, alkylsulfonyl or phenyloxy, with the proviso that when $R_{19}$ is aryl or substituted aryl, m is 2;

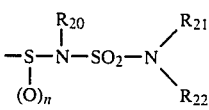 (g)

where n is 0, 1 or 2, $R_{20}$ is alkyl and $R_{21}$–$R_{22}$ are the same as $R_{17}$–$R_{18}$ as defined before;

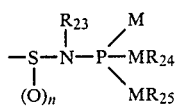 (h)

where n is 0, 1 or 2, M, independently, is S or O and $R_{23}$–$R_{25}$ independently represent alkyl or $R_{24}$ and $R_{25}$ together represent

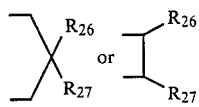

where $R_{26}$–$R_{27}$ independently represent hydrogen or alkyl;

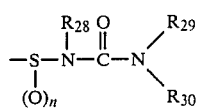 (i)

where n is 0, 1 or 2, $R_{28}$ is alkyl or aryl and $R_{29}$–$R_{30}$ independently represent hydrogen, alkyl, aryl or alkoxy;

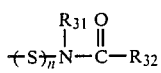 (j)

where n is 1 or 2, $R_{31}$ is alkyl and $R_{32}$ is fluoro, alkyl, aryl or aralkyl;

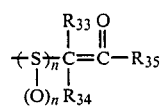 (k)

where m is 0, 1 or 2, n is 1 or 2 and $R_{33}$–$R_{35}$ independently represent hydrogen, alkyl or aryl;

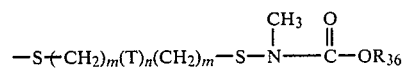 (l)

where T is O, S or —CH$_2$—, m is 1 or 2, n is 0 or 1 and $R_{36}$=$R_{13}$ as defined before;

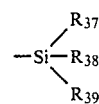 (m)

where $R_{37}$–$R_{39}$ are alkyl or aryl;

 (n)

where L represents alkyl, cyano, alkoxy, aryloxy, alkylthio, arylthio or —ON=CR$_{40}$R$_{41}$ where $R_{40}$–$R_{41}$ are the same as $R_{12}$–$R_{13}$ as defined before; or

 (o)

where V represents halogen, alkoxy or alkylthio and the pesticidal utility thereof.

As used throughout the instant specification and claims, the expressions "alkyl" and "alkoxy," unless otherwise defined, are inclusive of straight and branched chain carbon-carbon linkages of from 1 to about 22 carbon atoms, e.g., methyl, ethyl, n-propyl, isopropyl, n-butyl, isobutyl, sec-butyl, tert-butyl, hexyl, heptyl, octyl, decyl, or dodecyl, etc. The expressions "alkenyl" and "alkynyl," unless otherwise defined, include the corresponding unsaturated radicals. The expressions "cycloalkyl" includes cyclic alkanes of from 3 to about 8 carbon atoms, whereas "aryl" defines unsaturated ring systems of from 6 to about 12 carbon atoms. The term "halogen" includes chlorine, fluorine and bromine. The expression "polyoxyalkylene," unless otherwise defined, includes alkylene moieties of 1–4 carbon atoms and wherein the polyxoyalkylene moiety may contain up to 50 oxyalkylene repeating units.

It will be appreciated by those skilled in the art that the compounds of the present invention may be prepared in various salt forms and, as used herein, the expression "pesticidally acceptacle salts" is intended to include those salts capable of being formed with the instant compounds and substituted derivatives thereof in accordance with the invention without materially altering the chemical structure or pesticidal activity of the parent compounds. For example, alkali metal salts of carboxylic acid derivatives of the invention may be obtained by reaction with suitable bases, e.g., sodium hydroxide, potassium hydroxide, etc. Likewise, alkaline earth metal salts may be similarly obtained.

Similarly, quaternary salts of the amino derivatives of the invention may also be obtained, as well as acid addition salts, where necessary to, for instance, alter solubility properties.

It will be understood that in the structural formula depicting the compounds of the present invention all unsubstituted bonds are satisfied by hydrogen. It will further be apparent to those skilled in the art that the compounds of the present invention may exist in two geometric forms, the E and Z isomers (i.e., syn- and anti-isomers) around the carbon-nitrogen double bond. Both isomeric forms and their mixtures are encompassed within the scope of the present invention.

The hydroximino derivatives of the present invention, i.e., compounds of formula (I) where Y=hydrogen, are prepared according to the following methods.

Hydroximidate (oxabicyclo) compounds of the invention can be obtained, for example, by reaction of chlorosulfonyl isocyanate with appropriately substituted cyclic dienes to form N-chlorosulfonyl-β-lactams which readily rearrange to the (N-chlorosulfonyl-)imino-oxabicyclic intermediate (via cyclization through oxygen). See [*J. Org. Chem.* 41, 3583 (1976)], and [*J. Chem. Soc.* Perkin I, 874 (1977)] and the references cited therein. The thus obtained iminooxabicyclic intermediate is then reacted with hydroxylamine to yield the desired hydroximidate. The foregoing general reaction scheme is set forth below with substituent representations corresponding to those in formula (I). It will be recognized that, while the following scheme illustrates the formation of a compound of the present invention having a [2.2.1] bicyclic ring system, the above generally described process is followed to obtain compounds of the present inventon having, for example, a [3.2.1], [4.2.1], etc., bicyclic ring system. The specific bicyclic ring system obtained will, of course, be determined by the selection of the appropriate reactants (e.g., employing a cyclohexadiene reactant in place of the cyclopentadiene reactant below).

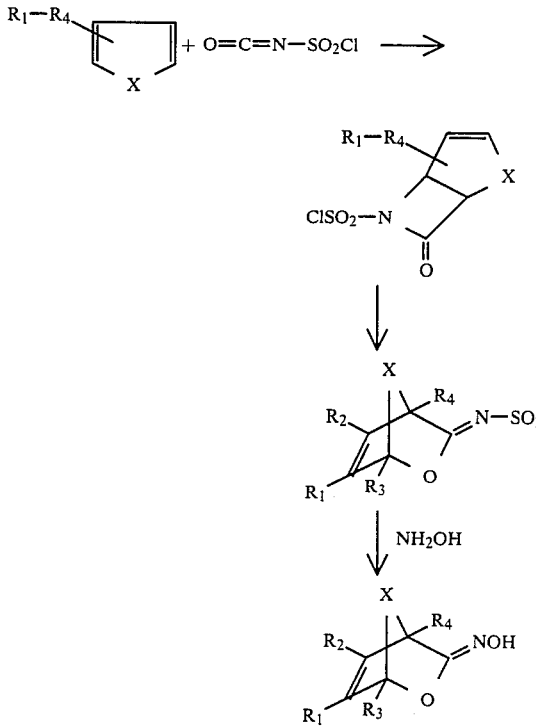

As alluded to previously, the bicyclic thiolhydroximidates of the present invention are obtained by a Diels-Alder reaction of certain thiocarbonyl compounds with appropriately substituted cyclic dienes under suitable cyclization conditions to obtain the initial adducts which are then reacted with hydroxylamine to afford the desired intermediates. The foregoing general reaction scheme is depicted below with substituent representations corresponding to those set forth previously in formula (I):

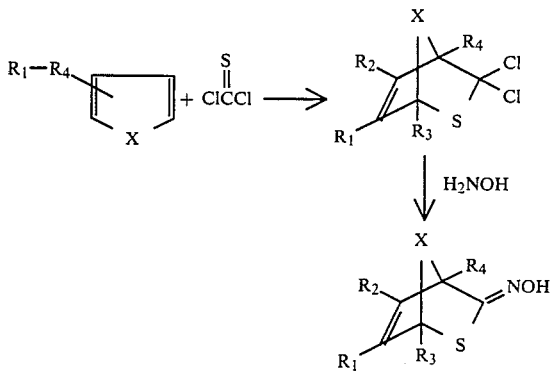

The bicyclic azahydroximidates of the present invention are prepared in a similar manner to the preparation of the oxa- and thiolhydroximidates previously described. More specifically, the appropriate 3-tosyl-2-azabicyclo intermediate [prepared by the procedure of *J. Organic Chemistry* 39, 564 (1974)] is treated with hydroxylamine to give the desired bicyclic azahydroximidate. Alternatively, conversion of the appropriate lactam to the corresponding thionolactam followed by treatment with hydroxylamine will also afford the desired azahydroximidate. The specific reactants, procedures and conditions are further illustrated in the examples.

The hydroximino intermediates can then be converted to the various carbamate derivatives embraced by formula (I) by any of several conventional methods. One preferred method involves the reaction of an isocyanate substituted with groups corresponding to $R_9$ or $R_{10}$ of formula (I) with the particular hydroximino intermediate. The hydroximino intermediate and isocyanate are reacted in an inert organic solvent at from about 0° C. to about 150° C., preferably from about 20° C. to about 80° C., and at a pressure from about 1 to 10 atmospheres, usually about 1 to about 3 atmospheres. Reaction pressures will be determined by reaction temperature, concentration and vapor pressure of the isocyanate.

Any inert organic solvent used in the reaction should not contain hydroxy, amino or other groups which will react with the isocyanate function. Useful inert solvents include aliphatic and aromatic hydrocarbons, e.g., hexane, heptane, octane, benzene, xylene; ethers such as diethyl ether, ethylpropyl ether, etc.; esters such as ethyl acetate, ethyl propionate; ketones such as acetone, methyl ethyl ketone and various chlorinated hydrocarbons such as methylene chloride, perchloroethylene and the like.

The reaction may be carried out in the presence of from about 0.1 to about 1.0 percent by weight, based on the weight of reactants, of a tertiary amine catalyst such as triethylamine, N,N-dimethylaniline or the like.

The molar ratio of isocyanate to hydroximino reactant can vary from about 0.1:1 to about 10:1. An equimolar amount or slight excess of isocyanate is preferred to insure complete reaction. Reaction times may also vary from a few minutes to several days with a usual reaction time of from about ½ to about 6 hours.

Another method for preparing such carbamate derivatives involves reaction of the hydroximino compound with phosgene to obtain the chloroformate which is reacted with an amine. A solution of the hydroximino derivative is generally dissolved in an inert solvent such as diethyl ether which is added slowly to a solution of phosgene dissolved in inert solvent in the presence of an HCl acceptor such as a tertiary amine. Reaction temperatures vary from about −30° C. to about 100° C. with usual temperatures of from about 0° C. to about 50° C. The resulting reaction mixture, a solution of the chloroformate in an inert organic solvent can be filtered to remove amine hydrochloride before reaction with an amine in step 2 of the reaction. The amine is added to the chloroformate solution in the presence of a suitable amine solvent such as water, at temperatures between about −40° C. to about 80° C. A larger than molar excess of amine can be used so that the amine acts both as a reactant and as an HCl acceptor and complete conversion of chloroformate is obtained. Alternatively, a separate HCl acceptor, such as a tertiary amine can be used.

It will also be appreciated by those skilled in the art that the carbamate derivatives of the present invention can be prepared by reaction of N-protected hydroxylamine with an appropriately substituted carbamylating agent, e.g.,

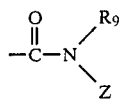

as defined before, deprotection of the resulting intermediate and reaction of the deprotected intermediate with, for example, the initial Diels-Alder adduct to obtain the products of formula (I).

The sulfenylated carbamates of the invention may be prepared from the carbamates and carbamate precursors obtained in accordance with the foregoing description by methods described, for example, in *Angewandte Chemie,* International Edition, 16, 735 (1977) and the references referred to therein, i J. Org. Chem. 43, 3953 (1978), *J. Agric. Food Chem.* 26, 550 (1978), U.S. Pat. Nos. 4,201,733, 4,148,910, 4,138,423 and 4,108,991.

Essentially, two methods have previously been employed for the preparation of such derivatives. In the first of these, an N-alkyl carbamate is allowed to react with a sulfenyl halide to yield the sulfenylated carbamate in accordance with the following reaction scheme:

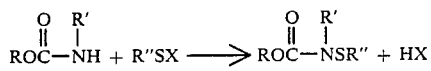

In the second method, the sulfenyl halide is allowed to react with an N-alkyl carbamyl halide to yield an intermediate N-alkyl-N-(substituted thio)-carbamyl halide which is then treated with the desired hydroxylic moiety to provide the carbamate.

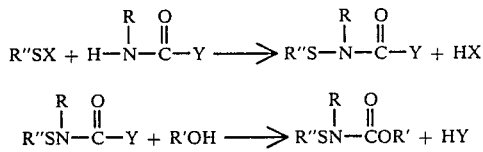

In each of the foregoing reactions, where HX or HY are generated, an acid acceptor is utilized to facilitate the reaction.

The foregoing sulfenylation reactions are normally conducted in an aprotic organic solvent. Illustrative of aprotic organic solvents which are suitable as reaction solvents in accordance with the present invention are those previously mentioned for use in connection with the preparation of the carbamate derivatives of the invention.

The acid acceptor utilized in carrying out the sulfenylation reaction may be either an organic or inorganic base. Organic bases useful as acid acceptors are tertiary amines, alkali metal alkoxides and the like. Bases such as sodium hydroxide, potassium hydroxide, sodium carbonate and the like are illustrative of inorganic bases suitable for use in the conduct of this reaction. Preferred acid acceptors are aromatic and aliphatic tertiary amines, such as triethylamine, pyridine, trimethylamine, 1,4-diazobicyclo[2.2.2]octane and the like.

When an inorganic base is used as the acid acceptor, phase transfer agents may be used to facilitate the transfer of the acid acceptor across the organic/inorganic phase interface. As useful phase transfer agents, there may be mentioned crown ether compounds, quaternary ammonium halide compounds and the like.

In these reactions, the reaction temperature may be varied between about −30° C. to approximately 130° C., preferably between 0° C. to about 75° C.

The sulfenylation reactions can be conducted at either substmospheric, atmospheric or superatmospheric pressures, but conventionally are conducted at atmospheric or autogenous pressure.

Reactants, intermediates or precursor compounds necessary in carrying out the reactions set forth herein are readily obtainable following conventional synthetic methods. For instance, N-methylcarbamyl fluoride may be prepared in accordance with the procedure detailed in *J. Org. Chem.* 43, 3953 (1978) as may N-(N,N-dialkylaminosulfenyl)-N-methylcarbamyl fluoride. N-[(N-alkyl-n-arylsulfonyl)aminosulfenyl]-N-methylcarbamyl fluoride is prepared according to the methods set forth in U.S. Pat. No. 4,148,910. The preparations of bis[(N-fluorocarbonyl-N-methyl)amino]sulfide, bis[(N-fluorocarbonyl-N-methyl)amino]disulfide and N-arenesulfenyl-N-methylcarbamyl fluoride are described in U.S. Pat. No. 3,639,471. N-(substituted-cyanoalkanesulfenyl and thiosulfenyl)-N-alkylcarbamyl halides are also described in U.S. Pat. No. 4,058,549.

The active compounds are well tolerated by plants, have a favorable level of toxicity to warm-blooded animals and can be used for combating arthropod pests, especially insects and arachnids, and nematode pests. They are active against normally sensitive and resistant species and against all or some stages of development, i.e., eggs, larvae, nymphs, cysts and adults. The above-mentioned pests include:

from the class of the Isopoda, for example, *Oniscus asellus, Armadillium vulgare* and *Cylisticus convexus;* from the class of the Diplopoda, for example, *Blaniulus guttulatus;* from the class of the Chilopoda, for example, Geophiluscarpophagus and Scutigera spp.; from the class of the Symphyla, for example, *Scutigerella immaculata;* from the order of the Thysanura, for example, *Lepisma saccharina;* from the order of the Collembola, for example, *Onychiurus armatus;* from the order of the Orthoptera, for example, *Blatta oreintalis, Periplaneta americana, Blattella germanica, Acheta domesticus,* Gryllotalpa spp., *Locusta migratoria migratorioides, Melanoplus differentialis* and *Schistocerca gregaria;* from the order of the Isoptera, for example, Reticulitermes spp.; from the order of the Thysanoptera, for example, *Hercinothrips femoralis* and *Thrips tabaci;* from the order of the Hemiptera, for example, Lygus spp., Dysdercus spp., *Nezara viridula;* from the order of the Homoptera, for example, *Bemesia tabaci,* Trialeurodes spp., Aphis spp., Macrosiphum spp., Myzus spp., Empoasca spp., *Nephotettix cincticeps,* Psylla spp.; from the order of the Lepidoptera, for example, *Pectinophora gossypiella, Plutella maculipennis, Malacosoma neustria, Porthetria dispar, Bucculatrix thurberiella,* Agrotis spp.; Euxoa spp., *Earias insulana,* Heliothis spp., *Prodenia litura,* Spodoptera spp., *Trichoplusia ni, Carpocapasa pomonella,* Pieris spp., chilo spp., *Pyrausta nubilalis, Ephestia kuehniella, Galleria mellonella, Choristoneura fumiferana,* and *Tortrix viridana;* from the order of the Coleoptera, for example, *Leptinotarsa decemlineata,* Diabrotica spp., *Epilachna varivestis, Oryzaephilus surinamensis,* Anthonomus spp., Sitophilus spp., *Hypera postica,* Dermestes spp., Trogoderma spp., Anthrenus spp., Attagenus spp., Lyctus spp., *Conotrachelus nenuphar, Po-*

*pillia japonica*, Ptinus spp., Tribolium spp., *Tenebrio molitor*, Agriotes spp., Conoderus sp., *Melolontha melolontha*, and *Costelytra zealandica;* from the order of the Hymenoptera, for example, Diprion spp., Hoplocampa spp., Lasius spp., *Monomorium pharanois*, Vespa spp., and *Caliroa cerasi;* from the order of the Diptera, for example, Aëdes spp., Anopheles spp., Culex spp., *Drosophila melanogaster*, Musca spp., Fannia spp., *Calliphora erythrocephala*, Lucilia spp., Chrysomya spp., Cuterebra spp., Gastrophilus spp., Hyppobosca spp., Stomoxys spp., Oestrus spp., Hypoderma spp., Tabanus spp., Tannia spp., *Oscinella frit, Pegomyia hyoscyami, Ceratitis capitata, Dacus oleae*, and *Tipula paludosa;* from the class of the Arachnida, for example, *Scorpio maurus* and *Latrodectus mactans;* from the order of the Acarina, for example, Acarus spp., Argas spp., Ornithodoros spp., *Dermanyssus gallinae, Eriophyes ribis*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., nd Tetranychus spp.; from the order of the Phylum nematoda, for example, species of the following genera Meloidogyne, Heterodera, Trichodorus, Xiphinema, Ditylenchus, Pratylenchus, Tylenchus, Radopholus, Longidorus, and Tylenchorhynchus.

Exemplary of preferred compounds for use in the arthropodicidal compositions and methods of the present invention are compounds of formula (II)

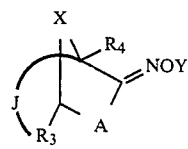    (II)

wherein
A represents S or O;
J represents the group

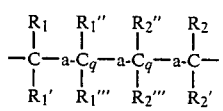

where q, independently, is 0 or 1, a, independently, is a single or double bond and $R_1$, $R_1'$, $R_1''$, $R_1'''$, $R_2$, $R_2'$, $R_2''$ and $R_2'''$ *are defined below;*
X is selected from

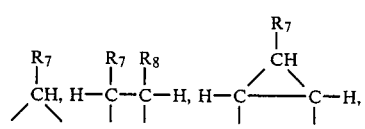,

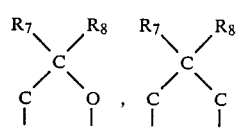

where $R_7$ and $R_8$ independently represent hydrogen or cyano;
$R_1$–$R_1'''$, inclusive, and $R_2$–$R_2'''$, inclusive, are hydrogen or when a is a double bond, $R_1$ and $R_2$, and in addition if q, independently in each case, is 1, $R_1''$ or $R_2''$, are independently hydrogen or halogen and $R_1'$, $R_2'$, $R_1'''$ or $R_2'''$ are absent;
$R_3$ and $R_4$ represent hydrogen, halogen, cyano or alkoxycarbonyl;
Y represents

    (1)

where $R_9$–$R_{10}$ independently represent hydrogen, alkyl, hydroxyalkyl, alkenyl or alkynyl; or

    (2)

where $R_9$ is the same as defined before and Z represents

    (a)

where n is 0, 1 or 2 and $R_{11}$ is phenyl or phenyl substituted with at least one member selected from halogen, alkyl, alkoxy, trifluoromethyl, nitro or cyano;

    (b)

where n is 0, 1 or 2, $R_{12}$ is alkyl and $R_{13}$ is alkyl, alkoxyalkyl or Q where Q-OY represents formula (II) as defined herein;

(c)    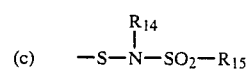

where $R_{14}$ is alkyl and $R_{15}$ is alkyl or

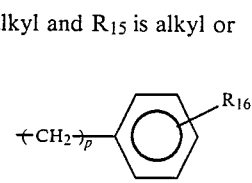

where p is 0–5 and $R_{16}$ is halogen, alkyl, trifluoromethyl, nitro, methoxy, cyano or dialkylamino;
(d) —S—NR$_{17}$R$_{18}$ where $R_{17}$–$R_{18}$ are alkyl, aryl or together with the nitrogen atom represent

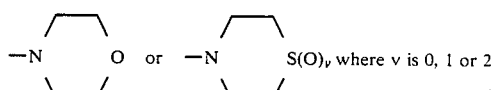

(e) —S)$_n$R$_{19}$ where n is 1 or 2 and $R_{19}$ is alkyl, cyanoalkyl or alkoxycarbonyl;

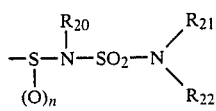
(f)

where n is 0, 1 or 2, $R_{20}$ is alkyl and $R_{21}$-$R_{22}$ are the same as $R_{17}$-$R_{18}$ as defined before;

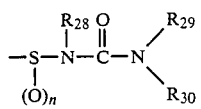
(g)

where n is 0, 1 or 2, $R_{28}$ is alkyl or aryl and $R_{29}$-$R_{30}$ independently represent hydrogen, alkyl, aryl or alkoxy; and

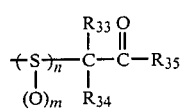
(h)

where m is 0, 1 or 2, n is 1 or 2 and $R_{33}$-$R_{35}$ independently represent hydrogen, alkyl or aryl.

As preferred compounds for use in the nematicidal compositions and methods of the present invention, there may be mentioned those compounds of Formula IV:

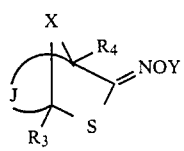
(IV)

wherein
J represents the group

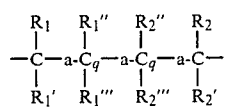

where q, independently, is 0 or 1, a, independently, is a single or double bond and $R_1$, $R_1'$, $R_1''$, $R_1'''$, $R_2$, $R_2'$, $R_2''$ and $R_2'''$ are defined below;
X is selected from

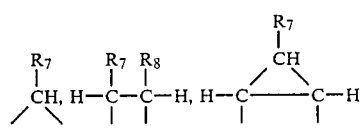

where $R_7$ and $R_8$ are hydrogen;
$R_1$-$R_1'''$, inclusive, and $R_2$-$R_2'''$, inclusive, are hydrogen or when a is a double bond, $R_1$ and $R_2$, and in addition if q, independently in each case, is 1, $R_1''$ or $R_2''$, are independently hydrogen or halogen and $R_1'$, $R_2'$, $R_1'''$ or $R_2'''$ are absent;
$R_3$ and $R_4$ represent hydrogen, halogen, cyano or alkoxycarbonyl;
Y represents

(1)

where $R_9$-$R_{10}$ independently represent hydrogen, alkyl, alkenyl or alkynyl; or

(2)

where $R_9$ is the same as defined before and Z represents

(a)

where n is 0, 1 or 2, $R_{11}$ is alkyl, phenyl or phenyl substituted with at least one member selected from halogen, alkyl, alkoxy or trifluoromethyl, nitro or cyano;

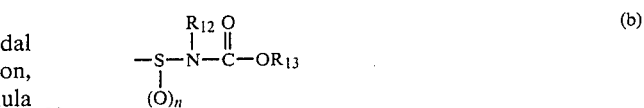
(b)

where n is 0, 1 or 2, $R_{12}$ is alkyl and $R_{13}$ is alkyl, alkoxyalkyl or Q where Q-OY represents Formula (IV) as defined herein;

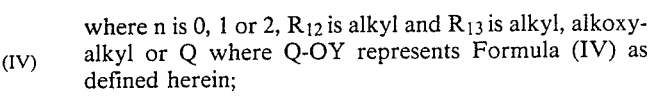
(c)

where $R_{14}$-$R_{15}$ are alkyl, aryl or substituted aryl with at least one substituent selected from halogen, alkyl, trifluoromethyl, nitro, methoxy, cyano or dialkylamino;
(d) —S—$NR_{17}R_{18}$ where $R_{17}$-$R_{18}$ are alkyl, aryl or together with the nitrogen atom represent

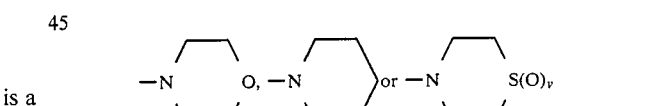

where v is 0, 1 or 2;

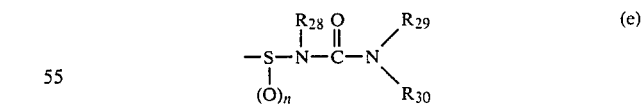
(e)

where n is 0, 1 or 2, $R_{28}$ is alkyl or aryl and $R_{29}$-$R_{30}$ independently represent hydrogen, alkyl, aryl or alkoxy; and

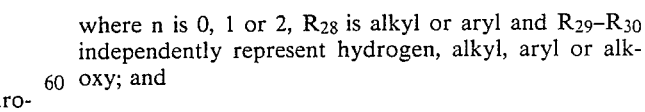
(f)

where m is 0, 1 or 2, n is 1 to 2 and $R_{33}$-$R_{35}$ independently represent hydrogen, alkyl or aryl.

In general, in the foregoing arthropodicidal and nematicidal compositions of the invention as well as the methods of selectively killing, combating or controlling such pests, the compounds of the invention, either alone or in admixture, will be applied to the pests or their habitat, including growing crops, in an arthropodicidally or nematicidally effective amount of the compound(s) within the range of from about 0.1 to 20 lb/A and, preferably, 0.25 to 1.5 lb/A, for arthropods and between about 0.125 to 20 lb/A and, preferably, about 0.25 to 4 lb/A for nematodes. The $LD_{50}$ of the carbamate ester derivatives of the invention in rats is generally in the range of 1.5 to 3 mg/kg, whereas the sulfenylated derivatives exhibit considerably reduced toxicities, i.e., up to a 15 fold decrease or greater.

The pesticidally active compounds in accordance with the present invention may be utilized in the form of formulations or compositions with appropriate dispersible pesticide carrier vehicles. As employed typically in the methods of the present invention, such compositions will contain between about 0.1 and 98 percent by weight, and usually between about 1 percent and 90 percent by weight of active compound. The heterobicyclic compounds of the invention are practically insoluble in water and only sparingly soluble in organic solvents. Accordingly, the compounds of the present invention are formulated in accordance with conventional practices in the form of, for example, wettable powders, dust or emulsifiable concentrates, water-based flowables, dispersible granules and the like. In such compositions, the active compound of the invention will be combined with suitable dispersing agents (e.g., lignin, sulfite waste liquors, methyl cellulose, etc.), surfactants, such as nonionic and anionic emulsifying agents (e.g., polyethylene oxide esters of fatty acids, polyethylene oxide ethers of fatty alcohols, alkyl sulfonates, aryl sulfonates, alkyl arylpolyglycol ethers, magnesium stearate, etc.) and appropriate solid pesticidally acceptable carriers or diluents (e.g., kaolins, alumina, silica, calcium carbonate, talc, etc.). In general, in preparing the active compound for incorporation in such formulations, the compound will be subjected to conventional comminuting treatment, such as air milling, hammer milling, ball milling, wet milling, etc., to obtain an average particle size of between about 3 to 5$\mu$. Depending upon the ultimate intended use and particular storage conditions, other optional adjuvants such as anticaking agents, antifoam agents, freeze-thaw depressants and the like may be incorporated in the compositions. Likewise, the compounds of the present invention may be employed in combination with other pesticidal agents, including, for example, insecticides, miticides, bactericides, fungicides, nematicides, herbicides, plant growth regulants, etc. Moreover, the compounds of the present invention have surprisingly demonstrated good activity for destroying parasitic worms. Thus their use as anthelmintic agents is also contemplated herein.

The following nonlimiting examples are afforded in order that those skilled in the art may more readily understand the present invention and specific preferred embodiments thereof with respect to the preparation of starting materials, intermediates and product compounds in accordance with the foregoing description. The assigned structures for the title compounds exemplified below as well as in compound Table 1 thereafter are consistent with nuclear magnetic resonance and infrared spectra and, where applicable, X-ray crystallography.

EXAMPLE 1

2-Thiabicyclo[2.2.1]hept-5-en-3-one oxime

A stirred solution of 33 g (0.5 m) of cyclopentadiene in 150 ml of petroleum ether was maintained at 0° to −10° C. as 23 g (0.2 m) of thiophosgene was added over 25 minutes. The colorless solution was stripped of volatiles. A solution of the residue in 200 ml of 1,2-dimethoxyethane was added over one hour at 0° C. to 2.0 m of hydroxylamine in 500 ml of water. The reaction mixture was stirred overnight and allowed to come to room temperature. A dried methylene chloride extract was stripped to yield a semi-solid residue which was purified by dry column chromatography (silica gel, ethyl ether:hexane::1:1). Two bands were observed. Extraction of each individually yielded 2.4 g of the less polar material, m. 87°–88° C. and 5.9 g of the more polar, m. 137°–137.5° C. The NMR and IR spectra indicate these to be the E and Z isomers of the title compound. The more polar material was identified as the Z isomer by X-ray crystallography.

EXAMPLE 2A

2-Thiabicyclo[2.2.2]oct-5-en-3-one oxime

Method A

A solution of 735 ml (7.3 m) of 1,3-cyclohexadiene in 650 ml of chloroform was stirred at 30°–50° C. while 600 ml (7.86 m) of thiophosgene was added over one hour. The mixture was stirred at 60°±5° C. for two hours, cooled, and added over 90 minutes at 25°–40° C. to a stirred mixture of hydroxylamine (from 2300 g (28 m) of hydroxylamine sulfate, 2700 ml of water, and 1130 g (27.8 m) of sodium hydroxide) and 800 ml of chloroform. The resulting mixture was stirred at 40°±5° C. for four hours, filtered, and the filter cake washed with chloroform. The chloroform layer from the combined filtrate and washings was separated, dried, and reduced in volume. After the addition of three liters of carbon tetrachloride, the solvent was distilled until a pot temperature of 75° C. was reached. The carbon tetrachloride solution was decanted from some gummy insolubles and allowed to cool to yield the title compound as a pale yellow solid, m. 118.5°–122° C.

Calc'd for $C_7N_9NOS$: C, 54.2; H, 5.9; N, 9.0; S, 20.7; Found: C, 53.7; H, 6.0; N, 9.0; S, 20.4.

Method B

A solution of 0.22 g (0.00085 m) of 3,3-bis-(1,2,4-triazol-1-yl)-2-thiabicyclo[2.2.2]oct-5-ene[J. Org. Chem. 45, 3713 (1981)] in 30 ml. of tert-butyl alcohol was treated with 0.75 g (0.011 m) of hydroxylamine hydrochloride. The mixture was heated under reflux, cooled, and partitioned between water and dichloromethane. The organic layer was dried over $MgSO_4$. The residue after removal of solvent was purified by thick layer chromatography to yield 0.036 g of product which was spectrometrically identical with that obtained in Method A of this example.

EXAMPLE 2B

Reaction of 2-thiabicyclo[2.2.2]oct-5-en-3-one with hydroxylamine

A solution of 1.4 g (0.01 m) of 2-thiabicyclo[2.2.2]oct-5-en-3-one [J. Org. Chem. 38, 2637 (1973)] in 30 ml of dimethoxyethane was added to a mixture of 3.01 g (0.04 m) of hydroxylamine hydrochloride and 2.27 g (0.02 m)

of sodium carbonate in 30 ml of water and 30 ml of dimethoxyethane at 0° C. The mixture was stirred at 0°–10° C. for 3 hours. TLC in ethyl acetate/hexane/ethanol (1:1:0.1) showed two intense spots (Rf 0.02 and 0.25). The mixture was extracted with methylene chloride. A white solid precipitated out in the aqueous layer. This was filtered and washed with water and methylene chloride to give 0.34 g of a compound identified by spectral analysis as 4,4'-(N-hydroxycarbamyl)cyclohex-2-enyl disulfide (2), m. 156°–158° C., Rf=0.02, H'-NMR (DMSO-d$_6$): δ 1.5–2.28 (4H, m, CH$_2$), 2.65–3.1 (1H, m, CHCO), 3.4–3.7 (1H, m, SCH), 5.78 (2H, s, CH), 8.73 (1H, s, NH), 10.2 (1H, s, OH); IR (KBr): 3150 (NHOH), 1610 cm$^{-1}$ (C=0).

The methylene chloride extract was dried with magnesium sulfate and filtered. After the solvent was removed at reduced pressure, the mixture was chromatographed on dry column silica gel using ethyl acetate/hexane/ethanol (1:1:0.1) as eluent to give a solid identified by NMR and IR spectroscopy as N-hydroxy-(4-mercaptocyclo-hex-2-enyl)carboxamide (1), m. 100°–101° C., Rf=0.25, H'-NMR (DMSO-d$_6$): δ1.95–2.2 (4H, m, CH$_2$), 2.6–3.05 (1H, m, CHCO), 3.3–3.8 (1H, m SCH), 5.3–6.0 (2H, m, CH), 8.7 (1H, s, NH), 10.2 (1H, s, OH); IR (KBr): 3200 (OH), 3025 (NH), 2550 (SH), 1612 cm$^{-1}$ (C=0). Compound 1 gradually converted to compound 2.

None of the 2-thiabicyclo[2.2.2]oct-5-en-3-one oxime was observed.

EXAMPLE 3

2-Thiabicyclo[2.2.2]oct-5-en-3-one oxime

Thiophosgene (296 g of 85%, 2.19 m) was added dropwise to a stirred solution of 167 g (2.08 m) of 1,3-cyclohexadiene in 500 ml of chloroform. The exothermic reaction caused the temperature to rise from 25° C. to 68° C. with refluxing of the solvent. After 45 minutes, the reaction mixture was cooled and added in portions over four hours to a stirred solution of hydroxylamine (prepared from 480 g (6.9 m) of hydroxylamine hydrochloride in 175 ml water by dropwise addition at 0° C. of a solution of 434 g of 89% potassium hydroxide (6.9 m) in 250 ml of water) at −15° C. After being stirred overnight, the reaction mixture was filtered and the filter cake washed with methylene chloride. The combined filtrate and washings were separated and the organic layer dried (MgSO$_4$) and reduced in volume at about 20 Torr. After addition of carbon tetrachloride to the residue, distillation of solvent was continued at atmospheric pressure until a pot temperature of 75° C. was attained. The hot mixture was filtered. Cooling of the gave a solid which was recrystallized from carbon tetrachloride to yield 271 g of the title compound.

EXAMPLE 4

Z-2-Thiabicyclo[2.2.1]hept-5-en-3-one oxime

Method A

A stirred solution of 14.5 g (0.22 m) of cyclopentadiene in 50 ml of petroleum ether was maintained at 0°±5° C. as 23 g (0.2 m) of thiophosgene was added over 40 minutes. The colorless solution was stripped of volatiles ona rotary evaporator. A solution of the residue in 100 ml of 1,2-dimethoxyethane was added at −5° C. to a stirred slurry of 55.8 g (0.8 m) of hydroxylamine hydrochloride, 115 g (0.4 m) of sodium carbonate decahydrate, 90 ml of water and 100 ml of 1,2-dimethoxyethane. The mixture was stirred overnight as the temperature was allowed to reach 25° C.

The upper liquid layer was separated, combined with a methylene chloride extract of the lower aqueous layer, washed, and dried (MgSO$_4$). A small portion was removed and stripped to dryness. The presence of E and Z isomers of the title compound was demonstrated by nuclear magnetic resonance and thin layer chromatography. The methylene chloride solution was treated with 2.5 ml of trifluoroacetic and allowed to stand at room temperature for four days. The solvent was stripped to yield 23.3 g of pale tan residue. This was confirmed as the Z isomer of the title compound by thin layer chromatography and nuclear magnetic resonance versus an authentic sample.

Method B

Thiocarbonyldiimidazole [9.0 g, (10.0 g of 90 percent technical material), 0.05 m] was dissolved in 250 ml of dichloromethane. The solution was treated with 10 ml of freshly cracked cyclopentadiene, and the mixture was refluxed for 4 hours. Evaporation of the solvent gave 16.8 g of a dark brown oil, the NMR of which was consistent with the structure, 3,3-bis(1-imidazolyl)-2-thiabicyclo[2.2.1]hept-5ene.

A portion (11.1 g, 0.033 m) of the oil was dissolved in 200 ml of absolute ethanol, and the solution was treated with 9.5 g of hydroxylamine hydrochloride. The mixture was refluxed for 2 hours. The solvent was evaporated, and the residue was partitioned between water and dichloromethane. The organic layer and 4 dichloromethane extracts of the aqueous layer were dried (MgSO$_4$), filtered with carbon and the solvent was evaporated. The residual brown oil was taken up in dichloromethane and hexane. Upon standing an oil was deposited. The solution was decanted, the solvent was evporated, and residue was triturated with dry ether. The ether soluble material was chromatographed on silica (preparative layer, 50 percent ether in hexanes). The purified material was eluted with acetone; there was obtained 1.51 g of material which was spectrometrically identical with the compound prepared by method 4A.

EXAMPLE 5

6,7-Dibromo-2-thiabicyclo[2.2.1]heptan-3-one oxime

A solution of 0.036 m of bromine in 167 ml of carbon tetrachloride was added over 30 minutes at 23°–30° C. to a stirred slurry of 5.0 g (0.035 m) of 2-thiabicyclo[2.2.1]hept-5-en-3-one oxime in 50 ml of carbon tetrachloride. After a further 30 minutes, the solvent was removed to yield 10.6 g of white solid residue, m. 168° C. Recrystallization from acetone gave 6.9 g of the title compound as a white solid m. 168° C. (dec.).

Calc'd for C$_6$H$_7$Br$_2$NOS: C, 23.9; H, 2.4; N, 4.7; Found: C, 24.0; H, 2,4; N, 4.7.

EXAMPLE 6

5(6)-Chloro-2-thiabicyclo[2.2.1]hept-5-en-3-one O[(methylamino)carbonyl]oxime To a solution of 5 g (0.035 m) of 2-thiabicyclo[2.2.1]hept-5-en-3-one oxime in 200 ml of methylene chloride was added, over 15 minutes at 25°–30° C., 5.7 g (0.042 m) of sulfuryl chloride. The mixture was stirred at room temperature for 45 minutes, then stripped to dryness to give 8.1 g of tan solid residue which was extracted with 300 ml of boiling methylene chloride. Cooling yielded 1.8 g of a dichloro-2-thiabicyclo[2.2.1]heptan-3-one oxime.

Calc'd for $C_6H_7Cl_2NOS$: C, 34.0; H, 3.3; N, 6.6; Found: C, 33.7; H, 3.2; N, 6.5.

A solution of 63 g (0.3 m) of the dichloro-oxime, 29 g (0.35 m) of dihydropyran, and 0.4 g of p-toluenesulfonic acid in 500 ml of methylene chloride was stirred for 16 hours at room temperature. The residue after removal of solvent was taken up in 400 ml of ether. The solution was neutralized with sodium bicarbonate, filtered, and stripped to yield an oil which was purified by dry column chromatography (silica gel; hexane:ether:acetone: 3:1:0.3) to yield 37.5 g of a diastereomeric mixture of dichlorobicyclo[2.2.1]heptan-3-one O-(2-tetrahydropyranyl)oxime. A portion of this was treated with ether to give a solid which was recrystallized from hexane-acetone. A white solid, m. 129°–131° C., was obtained.

Calc'd for $C_{11}H_{15}Cl_2NO_2S$: C, 44.6; H, 5.1: N, 4.7; Found: C, 44.5; H, 5.3; N, 4.8.

A solution of 19.5 (0.064 m) of the above protected tetrahydropyranyl-oxime in 250 ml of ether was treated under argon at $-10°$ C. with 14.4 g (0.13 m) of potassium ter-butoxide. The mixture was stirred 16 hours at 0° C. and four hours at room temperature, filtered, and the filtrate shaken with water. The dried ether layer was stripped to yield 9 g of yellow solid. A solution of 6.1 g of this in 200 ml of methanol was treated with 2 ml of concentrated hydrochloric acid, stirred for 16 hours, treated to neutrality with sodium bicarbonate and concentrated to dryness. The residue was taken up in methylene choride. The dried solution was stripped to yield 3.3 g of yellow oil. A solution of 2.8 g (0.016 m) of this oil, 2 ml of methyl isocyanate and one drop of triethylamine in 50 ml of methylene chloride was stirred at room temperature for 18 hours. The dark solution was treated with charcoal, filtered and stripped of solvent to give 3 g of yellow viscous oil. Dry column chromatographic purification (silica gel—acetone:hexane::2:3) provided 1.7 g of the title compound as a viscous oil which could not be induced to crystallize.

Calc'd for $C_8H_9ClN_2O_2S$: C, 41.3; H, 3.9; N, 12.0; Cl, 15.2; Found: C, 40.8; H, 4.5; N, 11.7; Cl, 15.3.

EXAMPLE 7

2-Oxabicyclo[2.2.2]oct-5-en-3-one oxime

To a 0° C. solution of hydroxylamine [from 4.2 g (0.06 m) of hydroxylamine hydrochloride, 8.6 g (0.03 m) of sodium carbonate decahydrate and 30 ml of water] in 50 ml of 1,2-dimethoxyethane was added dropwise, with stirring under nitrogen, 4.4 g (0.02 m) (N-chlorosulfonyl)imino-2-oxabicyclo[2.2.2]oct-5-ene [J. Chem. Soc., Perkin I, 874 (1977)] in 200 ml of 1,2-dimethoxyethane. After being stirred for 18 hours, the mixture was filtered to give 0.5 g of solid. Ether extraction of the filtrate yielded an additional 1.3 g of product. The combined solids were recrystallized from ethanol to provide the title compound as a white solid, m.p. 153°–4° C.

Calc'd for $C_9H_{12}N_2O_3$: C, 60.4; H, 6.5; N, 10.1; Found: C, 60.7; H, 6.8; N, 10.2.

EXAMPLE 8

2-Thiabicyclo[2.2.2]oct-5-en-3-one O-(2-tetrahydropyranyl)oxime

A solution of 10 g (0.06 m) of 2-thiabicyclo[2.2.2]oct-5-en-3-one oxime, 9 g (0.1 m) of 98% dihydropyran, and a catalytic amount of p-toluenesulfonic acid in 30 ml of methylene chloride was heated under reflux overnight. Sodium bicarbonate was added to neutrality. The residue after removal of solvent was purified by dry column chromatography (silica gel-ethyl acetate:hexane::1:1) to give 14.4 g of yellow solid. Recrystallization from ether-hexane yielded 10.1 g of the title compound as a white solid, m. 84°–5° C.

Calc'd for $C_{12}H_{17}NO_2S$: C, 60.2; H, 7.2; N, 5.9; Found: C, 60.0; H, 7.2; N, 5.9.

EXAMPLE 9

5,6-Dihydroxy-2-thiabicyclo[2.2.2]octan-3-one O-(2-tetrahydropyranyl)oxime

A mixture of 8 g (0.033 m) of the product of Example 8, 5.3 g (0.039 m) of N-methylmorpholine N-oxide, 4 ml of 2.5% osmium tetroxide in t-butanol, and 20 ml of acetone was stirred for four hours then extracted with ethylacetate. The organic solution was washed with brine, dried, and stripped to give 12 g of crude product which was purified by dry column chromatrography (silica gel, ethylacetate:hexane::1:1) to yield 5.8 g of the title compound as a white solid, M. 124°–6° C.

Calc'd for $C_{12}H_{19}NO_4S$: C, 52.7; H, 7.0; N, 5.1; Found: C, 52.6; H, 7.4; N, 5.0.

EXAMPLE 10

5,6-Dimethoxy-2-thiabicyclo[2.2.2]octan-3-one oxime

To a suspension of 1.4 g (0.03 m) of 60% sodium hydride in mineral oil was added a solution of 4 g (0.015 m) of the product of Example 9 in tetrahydrofuran. The mixture was stirred until gas evolution ceased, then cooled to 0° C. and treated with 2.3 g (0.015 m) of methyl iodide. This mixture was stirred at 40° C. After slow addition of a little methanol, followed by water, the mixture was extracted with methylene chloride. The organic solution was washed with brine, dried and stripped to give 6 g of oil which was purified by high performance liquid chromatography to yield an oil.

A solution of 1.8 g (0.0033 m) of this oil and 3 drops of 5N hydrochloric acid in 80 ml of methanol was heated under reflux overnight. Water was added. A methylene chloride extract of this mixture was dried and stripped to yield 1.25 g of the title compound as a solid.

EXAMPLE 11

2-Thiabicyclo[3.2.2]non-5-en-3-one oxime

A solution of 29 g (0.3 m) of 1,3-cycloheptadiene, 46 g (0.4 m) of thiophosgene, and 25 ml of cyclohexane was heated under reflux for 24 hours, then stripped of volatiles under reduced pressure. The oily residue was taken up in 150 ml of methylene chloride and stirred with 1.5 m of hydroxylamine in 200 ml of water at room temperature for three days. The separated organic layer was dried over magnesium sulfate and stripped to yield 26.7 g of viscous oil. Purification by dry column chromatography using silica gel and 1:4::ether:hexane as eluent. There was obtained 14 g of yellow solid. Recrystallization of 2 g portion from 1:1 ether-hexane yielded 1.4 g of the title compound as white crystals, m. 130°–132° C.

Calc'd for $C_8H_{11}NOS$: C, 56.8; H, 6.6; N, 8.3; S, 18.9; Found: C, 57.1; H, 6.7; N, 8.2; S, 18.5.

EXAMPLE 12

2-Thiabicyclo[3.2.2]nonan-3-one oxime

Air was passed through a stirred solution of 3.4 g (0.02 m) of the product of Example 11, 20 ml of 85% hydrazine hydrate, and 0.1 g of cupric acetate in 50 ml of isopropyl alcohol for six hours at room temperature. The mixture was poured into 300 ml of water. A methylene chloride extract was washed with water, dried over magnesium sulfate, and stripped to yield 3.7 g of solid residue. Dry column chromatography on silica gel using 1:4::ether:hexane yielded 3.1 g of the title compound as a white solid, m. 146°–8° C.

Calc'd for $C_8H_{13}NOS$: C, 56.1; H, 7.7; N, 8.2; S, 18.7; Found: C, 56.0; H, 7.9; N, 7.9; S, 18.6.

EXAMPLE 13

2-Thiabicyclo[2.2.1]heptan-3-one O-[(methylamino)carbonyl]oxime

A solution of 6.6 g (0.046 m) of 2-thiabicyclo[2.2.1]heptan-3-one oxime, 2.9 g (0.05 m) of methyl isocyanate, and 60 ml of methylene chloride was stirred at room temperature for 17 hours. Removal of solvent gave 9.1 g of yellow-tan solid which was purified by dry column chromatography on silica gel using ether-acetone as eluent. There was obtained 5.2 g of the title product as a cream colored solid, m. 121°–2° C.

Calc'd for $C_8H_{12}N_2O_2S$: C, 48.0; H, 6.0; N, 14.0; Found: C, 47.8; H, 6.1; N, 14.1.

EXAMPLE 14

2-Thiabicyclo[2.2.1]oct-5-en-3-one O-(aminocarbonyl)oxime

To a cold, stirred solution of 11 g (0.11 m) of phosgene in 20 ml of methylene chloride was added 12.1 g (0.1 m) of N,N-dimethylaniline. To this was added over one hour a solution of 14.1 g (0.0091 m) of 2-thiabicyclo[2.2.2]oct-5-en-3-one oxime in 100 ml of methylene chloride. The solution was stirred at 0° C. for two hours, then treated with a solution of 14.7 g of 29% aqueous ammonia in 40 ml of water. After a further 30 minutes, the organic layer was separated, washed twice with cold water, twice with cold dilute hydrochloric acid, and finally with water. The dried (MgSO₄) solution was stripped to give 16.6 g of solid residue. Purification by dry column chromatography over silica gel using ethyl acetate:cyclohexane::10:6 yielded 3.3 g of solid. The title compound was obtained as a white solid, m. 145°–7° C., by recrystallization from methylene chloride-petroleum ether.

Calc'd for $C_8H_{10}N_2O_2S$: C, 48.5; H, 5.1; N, 14.1; Found: C, 48.4; H, 5.2; N, 14.0.

EXAMPLE 15

2-Thiabicyclo[2.2.1]hept-5-en-3-one O-[(methylamino)carbonyl]oxime exo-2-oxide A solution of 18 g (0.091 m) of 2-thiabicyclo[2.2.1]hept-5-en-3-one O-[(methylamino)carbonyl]oxime in 300 ml of methylene chloride was treated over 15 minutes with a solution of 16.5 g (0.095 m) of 80.5% metachloroperoxybenzoic acid in 300 ml of methylene chloride. The temperature rose to 35° C. during the addition. After 15 minutes additional stirring, the reaction mixture was washed with 2×600 ml of 5% aqueous sodium bicarbonate. The aqueous washes were saturated with sodium chloride and extracted twice with methylene chloride. Stripping of the dried (MgSO₄) extract gave 6.8 g of solid residue. Recrystallization of a portion of this from acetone-hexane yielded the title compound as a pale tan solid, m. 118° C. (dec.).

Calc'd for $C_8H_{10}N_2O_3S$: C, 44.9; H, 4.7; N, 13.3; Found: C, 44.7; H, 4.7; N, 13.1.

EXAMPLE 16

2-Thiabicyclo[2.2.1]hept-5-en-3-one O-[(methylamino)carbonyl]oxime endo-2-oxide The procedure of Example 15 was repeated. The methylene chloride solution after the sodium bicarbonate wash was dried and concentrated to give 8.1 g of dark oil. Purification by dry column chromatography followed by medium pressure liquid chromatography gave 0.87 g of solid. Trituration with ether and hexane yielded 0.32 g of the title compound as a tan solid, m. 59°–77° C. (dec.).

Calc'd for $C_8H_{10}N_2O_3S$: C, 44.9; H, 4.7; N, 13.1; Found: C, 44.2; H, 5.1; N, 12.6.

EXAMPLE 17

2-Thiabicyclo[2.2.1]hept-5-en-3-one O-[(methylamino)carbonyl]oxime 2,2-dioxide To a stirred solution of 6.77 g (0.034 m) of 2-thiabicyclo[2.2.1]hept-5-en-3-one O-[(methylamino)carbonyl]oxime in 169 ml of methylene chloride was added a solution of 16.1 g (0.075 m) of 80.5% metachloroperoxybenzoic acid. The temperature rose to 33° C. After being heated at 35°–40° C. for five hours, the reaction mixture was cooled slowly without stirring to 0° C. The precipitated metachlorobenzoic acid was separated. The solution was stripped to dryness. After being slurried with two portions of ether, the residue was recrystallized from hexane-acetone to yield 1.6 g of the title compound as a white solid, m. 132° C. (dec.).

Calc'd for $C_8H_{10}N_2O_4S$: C, 41.7; H, 4.4; N, 12.2; Found: C, 41.3; H, 4.7; N, 12.0.

EXAMPLE 18

5,6-exo-Epoxy-2-thiabicyclo[2.2.1]heptan-3-one O-[(methylamino)carbonyl]oxime 2,2-dioxide A solution of 7.5 g (0.0325 m) of the product of Example 17 and 7.0 g (0.0325 m) of 80.5% metachloroperoxybenzoic acid in 730 ml of ethyl acetate was heated at reflux for 5 hours. After addition of a second equivalent of peracid, the mixture was heated for 3.5 hours, allowed to cool, and stripped to yield 19.9 g of white solid residue. This was slurried with two portions of ethyl ether to leave 5 g of crude product as residue. Purification by dry column chromatography followed by recrystallization from acetone-hexane gave 0.26 g of title compound as a white solid, m. 178°–9° C. (dec.).

Calc'd for $C_8H_{10}N_2O_5S$: C, 39.0; H, 4.1; N, 11.4; Found: C, 38.9; H, 4.3; N, 11.2.

EXAMPLE 19

5,6-Dihydroxy-2-thiabicyclo[2.2.2]octan-3-one O-[(methylamino)carbonyl]oxime To a solution of 6.5 g (0.048 m) of N-methylmorpholine N-oxide and 5.0 g (0.024 m) of 2-thiabicyclo[2.2.2]oct-5-en-3-one O-[(methylamino)carbonyl]oxime in 20 ml of acetone was added 15 ml of a 0.5% solution of osmium tetroxide in tert-butanol. The reaction mixture was stirred at room temperature for 48 hours, then treated with a slurry of 1 g sodium bisulfite, 15 g of magnesium silicate, and 50 ml of water. After being stirred for 30 minutes, the mixture was filtered. The filtrate was extracted with ethyl acetate, then with methylene chloride. Evaporation of the dried organic solution gave 4.8 g of viscous oil. Purification by dry column chromatography yielded 3.5 g of the title compound as a white solid, m. 123°–5° C.

Calc'd for $C_9H_{14}N_2O_4S$: C, 43.9; H, 5.7; N, 11.4; Found: C, 43.8; H, 6.1; N, 11.3.

EXAMPLE 20

5,6-isoPropylidenedioxy-2-thiabicyclo[2.2.2]octan-3-one O-[(methylamino)-carbonyl]oxime A mixture of 1 g (0.004 m) of the product of Example 19, 2 ml of acetone, 0.13 g of p-toluenesulfonic acid, and 50 ml of methylene chloride was heated overnight at reflux. After addition of 0.03 g of sodium acetate, the mixture was stirred for 30 minutes, filtered, and stripped to yield 1.26 g of white solid residue. Purification by dry column chromatography over silica gel using ethyl acetate:hexane:ethanol::1:1:0.1 gave 1 g of the title compound as a white solid, m. 126°–8° C.

Calc'd for $C_{12}H_{18}N_2O_4S$: C, 50.3; H, 6.3; N, 9.8; Found: C, 50.2; H, 6.5; N, 9.7.

EXAMPLE 21

2-Thiabicyclo[2.2.2]oct-5-en-3-one O-[(t-butyldimethyl)silyl]oxime

A solution of 15.5 g (0.1 m) of 2-thiabicyclo[2.2.2]oct-5-en-3-one oxime, 18.1 g (0.12 m) of t-butyldimethylsilyl chloride and 17.0 g (0.25 m) of imidazole in 300 ml of ethyl ether was stirred overnight at room temperature, then filtered. The filtrate was washed with saturated brine, dried, and stripped to yield 7.2 g of solid residue which was purified by dry column chromatography to give 6.4 g of the title compound as a white solid, m. 78°–9° C.

Calc'd for $C_{13}H_{23}NOSSi$: C, 57.8; H, 8.6; N, 5.2; Found: C, 57.6; H, 8.8; N, 5.2.

EXAMPLE 22

N,N'-thiobis[(methylimino)carbonyloxy]-2-thiabicyclo[2.2.2]octan-3-imine

A solution of 10.7 g (0.05 m) of 2-thiabicyclo[2.2.2]octan-3-one O-[(methylamino)carbonyl]oxime in 30 ml of pyridine was cooled at 0° C. as 3.8 g (0.028 m) of sulfur monochloride was added over five minutes. The mixture was stirred at 0° C. overnight, poured onto ice and water, and filtered. The filter cake was washed with cold dilute hydrochloric acid, then with water and dried to yield 12.2 g of solid, m. 158°–62° C. Recrystallization from hot 2-butanone gave the title compound as an off-white solid, m. 174°–6° C. (dec.).

Calc'd for $C_{18}H_{26}N_4O_4S_3$: C, 47.1; H, 5.7; N, 12.2; Found: C, 47.3; H, 5.9; N, 12.3.

EXAMPLE 23

2-Thiabicyclo[2.2.2]octan-3-one O-[N-methyl-N-([N-methyl-N-(butoxycarbonyl)amino]thio)carbonyl]oxime To a stirred solution of 10.7 g (0.05 m) 2-thiabicyclo[2.2.2]octan-3-one O-[(methylamino)carbonyl]oxime and 4.4 g (0.055 m) of pyridine in 100 ml of methylene chloride at 0° C. was added 10.9 g (0.055 m) of butyl N-chlorothio-N-methylcarbamate. After being stirred overnight as it was allowed to come to room temperature, the reaction mixture was diluted with 200 ml of ethyl ether, then washed with three 150 ml portions of water. The organic solution was dried over magnesium sulfate, filtered, and the filtrate stripped of solvent. The residue was purified by dry column chromatography (silica gel, hexane:ethyl ether::1:1) to yield 12 g of the title substance as a white powder, m. 77.5°–80° C.

Calc'd for $C_{15}H_{25}N_3O_4S_2$: C, 48.0; H, 6.7; N, 11.2; Found: C, 48.0; H, 6.9; N, 11.2.

EXAMPLE 24

2-Thiabicyclo[2.2.2]octan-3-one O-[N-(N-fluorocarbonyl-N-methyl)aminothio]-N-methylaminocarbonyloxime To a cooled (−10° C.) solution of 18.4 g (0.1 m) of bis[N-fluorocarbonyl-N-methyl)amino]sulfide and 15.7 g (0.1 m) of 2-thiabicyclo[2.2.2]octan-3-one oxime in 200 ml of methylene chloride was added, over 30 minutes, 14.0 ml (0.1 m) of triethylamine. After being stirred at −10° C. for 40 minutes, the reaction mixture was poured directly onto a silica gel dry column which was developed with ether:hexane::1:1. This gave 26.4 g of solid. Purification on HPLC and dry column chromatography using ether yielded the title compound as a solid, m. 98°–100° C.

Calc'd for $C_{11}H_{16}FN_3O_3S_2$: C, 41.1; H, 5.0; N, 13.1; S, 20.0; Found: C, 41.2; H, 5.3; N, 13.3; S, 20.1.

EXAMPLE 25

2-Thiabicyclo[2.2.2]octan-3-one O-(N-methyl)-N[N-methyl-N-(1-methylthioethylideneamino-oxycarbonyl)aminothio]aminocarbonyloxime To a stirred solution of 3.2 g (0.01 m) of the product of Example 24 and 1.05 g (0.01 m) of methylthioacetohydroxamate in 50 ml of methylene chloride was added 1.4 ml (0.01 m) of triethylamine. The reaction mixture was stirred overnight, washed with water, dried and stripped to give 4.3 g of a white solid. Purification by dry column chromatography (silica gel, ether) yielded 3.25 g of the title compound as a white solid, m. 176°–9° C.

Calc'd for $C_{14}H_{22}N_4O_4S_3$: C, 41.4; H, 5.5; N, 13.8; S, 23.7; Found: C, 41.2; H, 5.8; N, 13.7; S, 23.4.

EXAMPLE 26

2-Thiabicyclo[2.2.1]hept-5-en-3-one O-[N-methyl-N-(2-cyano-2-propylthiosulfenyl)-]aminocarbonyloxime A solution of 6.1 g (0.043 m) of 2-thiabicyclo[2.2.1]hept-5-en-3-one oxime and 9.0 g (0.043 m) of N-methyl-N(2-cyano-2-propylthiosulfenyl)aminocarbonyl chloride in 200 ml of methylene chloride was treated with 4.4 g (0.43 m) of triethylamine. After being stirred overnight, the mixture was washed with three portions of water, dried, and stripped to give 14.6 g of brown gum. Purification by dry column chromatography (silica gel, ether:hexane::9:1) yielded 8 g of the title compound as an off-white solid, m. 76°–8° C.

Calc'd for $C_{12}H_{15}N_3O_2S_3$: C, 43.8; H, 4.6; N, 12.8; Found: C, 43.5; H, 4.8; N, 12.6.

EXAMPLE 27

2-Thiabicyclo[2.2.1]hept-5-en-3-one O-(N-methyl)-[(N-methyl)-N-(p-toluenesulfonyl)aminosulfenyl]aminocarbonyloxime A solution of 6.8 g (0.048 m) of 2-thiabicyclo[2.2.1]-hept-5-en-3-one oxime and 14.0 g (0.048 m) of (N-methyl)-[N-methyl-N-(p-toluenesulfonyl)amino]sulfenylaminocarbonyl fluoride in 100 ml of methylene chloride was treated with 4.8 g (0.048 m) of triethylamine. After being stirred for 72 hours, the solution was washed with water, dried, and stripped to give 13.2 g of dark viscous residue. Purification by dry column chromatography (silica gel, ethyl ether) yielded 6 g of the title compound as a brown solid, m. 120°–122° C.

Calc'd for $C_{16}H_{19}N_3O_4S_3$: C, 46.5; H, 4.7; N, 10.2; Found: C, 46.2; H, 4.7; N, 10.2.

EXAMPLE 28

2-Thiabicyclo[2.2.2]octan-3-one O-(N-methyl)-N-(3-trifluoromethylphenylthio)-aminocarbonyloxime To a stirred suspension of 5.36 g (0.025 m) of 2-thiabicyclo[2.2.2]-octan-3-one O[(methylamino)carbonyl]oxime in 50 ml of carbon tetrachloride was added 3.96 g (0.025 m) of 1,5-diazabicyclo[5.4.0]-undec-5-ene. The reaction mixture was cooled at −10° C. during the addition of 6.38 g (0.03 m) of 3-trifluorobenzenesulfenyl chloride in 25 ml of carbon tetrachloride. After being stirred for 18 hours, the reaction mixture was filtered. Stripping of the filtrate gave 6 g of an oil which was purified by dry column chromatography (silica gel, ether) to give 3.1 g of solid. Recrystallization from ethanol yielded the title compound as a white solid, m. 60°–2° C.

Calc'd for $C_{16}H_{17}F_3N_2O_2S_2$: C, 49.2; H, 4.4; N, 7.2; Found: C, 49.1; H, 4.7; N, 7.1.

EXAMPLE 29A

4-Cyano-2-thiabicyclo[2.2.2]oct-5-en-3-one O-(N-methyl)-N(4-t-butylphenylthio)aminocarbonyloxime To a stirred mixture of 5.9 g (0.03 m) of 4-cyano-2-thiabicyclo-[2.2.2]oct-5-en-3-one oxime and 7.24 g (0.03 m) of N(p-t-butylphenylthio)-N-methylcarbamyl fluoride in 150 ml of methylene chloride was added 3.04 g of triethylamine in 50 ml of methylene chloride. After being stirred for 72 hours, the reaction mixture was stripped. Purification of the residue by dry column chromatography gave a solid which was recrystallized from ethanol to yield 3.8 g of the title compound as a white solid, m. 148°–9° C.

Calc'd for $C_{20}H_{23}N_3O_2S_2$: C, 59.8; H, 5,8; N, 10.5; Found: C, 59.8; H, 6.0; N, 10.6.

EXAMPLE 29B

2Thiabicyclo[2.2.2]oct-5-ene-3-one O-(N-methyl)-N-(4-tertbutylphenylthio)-aminocarbonyl oxime, hydrate A flame dried 3-neck flask was equipped with a gas inlet tube, mechanical stirrer and injection septum. Under nitrogen atmosphere, 4.37 g (0.03 m) 2,2,6,6-tetramethylpiperidine was dissolved in 100 ml THF (distilled from LAH) with stirring, while 18.8 ml of a 1.6 molar (in hexane) solution on n-butyllithium was injected through the septum. The reaction mixture assumed a yellow color. Stirring was continued for 10 minutes, after which the reaction mixture was cooled to −78°. Over a two-minute period, a solution of 6.38 g (0.03 m) of 2-thiabicyclo[2.2.2]oct-5-ene-3-one O-(N-methylaminocarbonyl)oxime in 100 mL THF was added. Stirring was continued for 5 minutes, 6.03 g (0.03 m) p-t-butylbenzenesulfenyl chloride in 100 ml tetrahydrofuran was added dropwise during 15 minutes, and the reaction mixture was allowed slowly to come to ambient temperature over an 18-hour period. The reaction mixture was then quenched with saturated aqueous ammonium chloride, extracted with 300 ml ether and water washed five times. The ether extract was dried over $MgSO_4$, filtered and the solvent removed under reduced pressure to give 9 g of a brown oil which was chromatographed on a silica gel dry column (ether) to give 2.51 g (21 percent) of the title compound as a yellow oil. Crystallization was induced by trituration with ether. Recrystallization from ethanol afforded pure product (0.6 g), m. 119°–120° C.

Calc'd for $C_{19}H_{24}N_2O_2S_2 H_2O$: C, 57.8; H, 6.6; N, 7.1; Found: C, 57.8; H, 6.3; N, 7.1.

EXAMPLE 30

N,N'-dithiobis[(methylimino)carbonyloxy]-2-thiabicyclo[2.2.1]hept-5-en-3-imine

A solution of 10.1 g (0.1 m) of triethylamine in 25 ml of methylene chloride was added over 30 minutes at 0° C. to a stirred solution of 14.1 g (0.1 m) of 2-thiabicyclo[2.2.1]hept-5-en-3-one oxime and 10.8 g (0.05 m) of bis[(N-methyl-N-fluorocarbonyl)amino]disulfide in 200 ml of methylene chloride. The mixture was allowed to warm to room temperature, stirred for 20 hours, and stripped to give a semisolid residue. After being passed through a short column of silica gel (ethyl acetate as eluent), the material was purified by dry column chromatography (silica gel, methylene chloride:acetone::95:5) to give a brown syrup. Trituration with ether gave 10.2 g of the title compound as a tan solid, m. 148°–150° C. (dec.).

Calc'd for $C_{16}H_{18}N_4O_4S_4$: C, 41.9; H, 4.0; N, 12.2; S, 28.0; Found: C, 41.9; H, 4.2; N, 12.1; S, 27.8.

EXAMPLE 296

2-Azabicyclo[2.2.1]hept-5-en-3-one oxime

To a solution of hydroxylamine (from 2.1 g (0.03 m) of hydroxylamine hydrochloride, 4.3 g (0.015 m) of sodium carbonate, 10 ml of water and 200 ml of tetrahydrofuran) at 0° C. was added 5.16 g (0.021 m) of 3-tosyl-2-azabicyclo[2.2.1]hepta-2,5-diene (prepared by the procedure of *J. Organic Chemistry*, 39, 564 (1974)) in 50 ml of tetrahydrofuran. After being stirred overnight, during which time the temperature was allowed to warm to 25° C., the organic layer was separated, dried, and stripped of solvent. Purification of the residue by chromatography (silica gel: 1:1::dichloromethane:ethyl acetate) gave 0.8 g of material whose spectra were consistent with the title structure.

EXAMPLE 297

2-Methyl-2-azabicyclo[2.2.2]octan-3-one oxime

A slurry of 33.0 g (0.218 m) of 4-(methylamino)benzoic acid and 4.0 g of 5% rhodium on alumina catalyst in 350 ml of water was shaken under 1500 psig of hydrogen for 24 hours. The insolubles were removed by filtration. The slurry from partial removal of water under reduced pressure was diluted with 300 ml of N,N-dimethylformamide and chilled. The precipitated solid was filtered, washed with several portions of cold acetone, and dried to yield 23 g (75%) of 4-(methylamino)cyclohexanecarboxylic acid.

The crude acid in 200 ml of diphenyl ether was heated at 230°-250° C. for 20 minutes with removal of water. Removal of the diphenylether under reduced pressure gave 10.6 g (52%) of 2-methyl-2- azabicyclo[2.2.2]octan-3-one.

A solution of this in 100 ml of toluene was added to a mixture of 28.3 g (0.07 m) of 4-methoxyphenylthionophosphine sulfide in 100 ml of toluene. After 3 hours under reflux, the cooled mixture was filtered and the filtrate evaporated to dryness. The oily residue was purified by column chromatography (silica gel: 3:1::ether:petroleum ether) to yield 8.8 g of 2-methyl-2-azabicyclo[2.2.2]octan-3-thione.

A solution of the thione in 50 ml of acetone was added to 80.9 g (0.57 m) of methyl iodide under nitrogen at room temperature. After being stirred overnight, the mixture was chilled and filtered under nitrogen to give 10.6 g of solid. A partial solution of this solid in 75 ml of chloroform was added dropwise to a stirred solution of hydroxylamine (from 5 g (0.072 m) hydroxylamine hydrochloride, 15.5 g (0.054 m) of hydrated sodium carbonate, 10 ml of water, and 150 ml of chloroform) at 0° C. After 6 hours, during which the mixture was allowed to warm to room temperature, the organic phase was separated, dried and stripped to yield 4.4 g of residue whose spectra were consistent with the title structure.

The following compounds were prepared using the foregoing synthesis procedures with appropriate selection of substituted dienes, dienophiles and carbamylating agents to obtain the derivatives of formula I set forth in Tables I-VI.

TABLE I

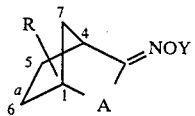

| EX. NO. | A | a | R | Y | MELTING RANGE °C. | CALCULATED C | CALCULATED H | CALCULATED N | FOUND C | FOUND H | FOUND N |
|---|---|---|---|---|---|---|---|---|---|---|---|
| 31 | S | double | H | C(=O)NHCH$_3$ | 118–119 | 48.5 | 5.1 | 14.1 | 48.5 | 5.2 | 13.8 |
| 32 | S | double | H | C(=O)NHCH$_3$ | 89–91 | 48.5 | 5.1 | 14.1 | 48.6 | 5.2 | 14.2 |
| 34 | No Example | | | | | | | | | | |
| 58 | S | double | H | C(=O)N(CH$_3$)S—N(CH$_3$)C(=O)Q | 156 | 45.1 | 4.2 | 13.1 | 44.8 | 4.4 | 12.9 |
| 70 | S | double | H | C(=O)N(CH$_3$)S—C$_6$H$_4$C(CH$_3$)$_3$—4 | 99–100 | 59.6 | 6.1 | 7.7 | 59.7 | 6.2 | 7.7 |
| 78 | S | double | H | C(=O)N(CH$_3$)S—N(CH$_3$)SO$_2$N(CH$_3$)$_2$ | 109–110 | 36.0 | 5.0 | 15.3 | 36.0 | 5.1 | 15.3 |
| 81 | S | double | H | C(=O)N(CH$_3$)S—C$_6$H$_5$ | oil | 54.9 | 4.6 | 9.1 | 54.5 | 4.8 | 8.7 |
| 89 | S | double | H | C(=O)N(CH$_3$)S—NCH$_2$CH$_2$OCH$_2$CH$_2$ | 115–116 | 45.7 | 5.4 | 13.3 | 45.5 | 5.3 | 13.2 |
| 101 | S | double | H | C(=O)N(CH$_3$)SC$_6$H$_4$CH$_3$—2 | 115–116 | 56.2 | 5.0 | 8.7 | 56.0 | 5.3 | 8.5 |
| 112 | S | double | H | C(=O)N(CH$_3$)SC$_6$H$_4$Cl—4 | 64–68 | 47.3 | 3.8 | 8.2 | 49.1 | 4.0 | 8.1 |
| 117 | S | double | H | C(=O)N(CH$_3$)SC$_6$H$_4$CH$_3$—4 | 73–74 | 56.2 | 5.0 | 8.7 | 56.2 | 5.2 | 8.6 |
| 122 | S | single | 6,7-(Br)$_2$ | C(=O)NHCH$_3$ | 163 | 26.8 | 2.8 | 7.8 | 27.1 | 3.0 | 7.9 |
| 125 | S | double | H | C(=O)N(CH$_3$)SN(CH$_2$CH$_2$CH$_3$)SO$_2$C$_6$H$_4$—CH$_3$—4 | 85–87 | 50.0 | 5.3 | 9.5 | 50.0 | 5.6 | 9.8 |
| 126 | S | double | H | C(=O)NHCH$_2$CH$_2$CH$_3$ | 69–71 | 53.1 | 6.2 | 12.4 | 53.0 | 6.5 | 12.3 |
| 128 | S | double | H | C(=O)NHCH$_2$CH$_2$CH$_3$ | 72–75 | 53.1 | 6.2 | 12.4 | 53.0 | 6.3 | 12.5 |
| 129 | S | double | H | C(=O)N(CH$_3$)SN(C$_4$H$_9$—n)SO$_2$C$_6$H$_4$CH$_3$—4 | oil | 50.1 | 5.5 | 9.2 | 50.3 | 5.9 | 9.0 |
| 130 | S | single | 5,6-[C$_6$H$_5$C(=O)O]$_2$ | C(=O)NHCH$_3$ | 150 | 60.0 | 4.6 | 6.4 | 59.8 | 4.6 | 6.2 |
| 131 | S | single | 5,6-[CH$_3$C(=O)O]$_2$ | C(=O)NHCH$_3$ | 149–150 | 45.6 | 5.1 | 8.9 | 45.6 | 5.2 | 8.9 |
| 135 | S | double | H | C(=O)N(CH$_3$)SC$_6$H$_4$Br—4 | 67–69 | 43.6 | 3.4 | 7.3 | 43.4 | 3.4 | 7.1 |
| 137 | S | single | 5,6-[CH$_3$NHC(=O)O]$_2$ | C(=O)NHCH$_3$ | 200–202 | 41.6 | 5.2 | 16.2 | 41.5 | 5.4 | 16.0 |
| 138 | S | single | 5,6-OCH$_2$O— | C(=O)NHCH$_3$ | 190–192 | 41.9 | 3.9 | 10.8 | 42.0 | 4.0 | 10.8 |
| 139 | S | double | H | C(=O)N(CH$_3$)SN(CH(CH$_3$)$_2$)SO$_2$C$_6$H$_4$—CH$_3$—4 | 155–157 | 49.0 | 5.2 | 9.5 | 48.8 | 5.4 | 9.6 |
| 143 | S | single | 5,6-Cl$_2$ | H | 137–138 | 34.0 | 3.3 | 6.6 | 33.7 | 3.2 | 6.5 |
| 147 | S | single | 5(6)-CH$_3$NH—C(=O)O—6(5)-(HO)— | C(=O)NHCH$_3$ | 60–80 | 41.5 | 5.2 | 14.5 | 41.9 | 5.9 | 14.2 |
| 148 | S | double | H | C(=O)N(CH$_3$)SC$_6$H$_4$Cl—2 | 112–113 | 49.3 | 3.8 | 8.2 | 49.2 | 4.1 | 8.1 |
| 149 | S | double | H | C(=O)N(CH$_3$)SN(CH$_2$CH$_2$CH$_3$)SO$_2$C$_6$H$_5$ | syrup | 47.8 | 4.9 | 9.8 | 48.0 | 5.3 | 9.6 |
| 152 | S | single | 5(6)C$_6$H$_5$C(=O)O—6(5)-(HO) | C(=O)NHCH$_3$ | 187–189 | 53.6 | 4.8 | 8.3 | 51.6 | 4.8 | 8.0 |
| 153 | S | single | 5(6)-HO—6(5)-C$_6$H$_5$C(=O)—O | C(=O)NHCH$_3$ | 162–165 | 53.6 | 4.8 | 8.3 | 52.2 | 4.8 | 8.1 |
| 154 | S | single | H | H | 100–102 | 50.3 | 6.3 | 9.8 | 50.4 | 6.6 | 9.9 |
| 157 | S | double | H | C(=O)NHCH$_2$CH=CH$_2$ | 110–111 | 53.6 | 5.4 | 12.5 | 53.5 | 5.5 | 12.5 |
| 160 | S | single | 5,6-(HO)$_2$ | C(=O)NHCH$_3$ | 98–101 | 41.5 | 5.5 | 11.8 | 41.5 | 5.6 | 11.8 |
| 161 | S | double | 7-Br | C(=O)NHCH$_3$ | 87–92 | 34.7 | 3.3 | 10.1 | 34.8 | 3.4 | 10.0 |
| 167 | S | double | H | C(=O)N(CH$_3$)SN(CH$_2$CH$_2$CH$_3$)SO$_2$—C$_6$H$_4$Cl—4 | 108–111 | 44.2 | 4.4 | 9.1 | 44.5 | 4.5 | 9.3 |

TABLE I-continued

| EX. NO. A | a | R | Y | MELTING RANGE °C. | CALCULATED C | H | N | FOUND C | H | N |
|---|---|---|---|---|---|---|---|---|---|---|
| 170 S | double | H | C(=O)N(CH$_3$)SN(CH$_2$CH$_2$CH$_3$)SO$_2$CH$_3$ | 91–94 | 39.4 | 5.2 | 11.5 | 39.3 | 5.6 | 11.4 |
| 172 S | double | H | C(=O)N(CH$_3$)SN(CH$_3$)C(=O)OCH$_3$ | 93–95 | 41.6 | 4.8 | 13.2 | 41.7 | 4.9 | 13.2 |
| 178 S | double | H | C(=O)N(CH$_3$)$_2$ | 87–95 | 50.9 | 5.7 | 13.2 | 50.8 | 6.1 | 13.3 |
| 182 S | single | H | C(=O)N(CH$_3$)SN—(CH(CH$_3$)$_2$)SO$_2$C$_6$H$_4$CH$_3$—4 | 139–140.5 | 48.7 | 5.7 | 9.5 | 48.4 | 5.7 | 9.8 |
| 183 S | double | 5(6)Cl | C(=O)NHCH$_3$ | oil | 41.3 | 3.9 | 12.0 | 40.8 | 4.5 | 11.7 |
| 185 S | double | H | C(=O)NH$_2$ | 126–127 | 45.6 | 4.4 | 15.2 | 45.7 | 4.5 | 15.3 |
| 187 S | double | H | C(=O)N(CH$_3$)SN(CH(CH$_3$)$_2$)SO$_2$N(CH$_3$)$_2$ | 112–114 | 39.6 | 5.6 | 14.2 | 39.5 | 5.9 | 13.9 |
| 191 S | double | H | C(=O)NH$_2$ | 135–138 | 45.6 | 4.4 | 15.2 | 45.4 | 4.4 | 15.2 |
| 209 S | double | 4-C(=O)OCH$_3$ | C(=O)NHCH$_3$ | 112–113 | 46.9 | 4.7 | 10.9 | 46.8 | 4.4 | 11.0 |
| 212 S | double | H | C(=O)N(CH$_3$)SN(C$_{12}$H$_{25}$n)SO$_2$N(CH$_3$)$_2$ | 82–84 | 50.7 | 7.8 | 10.8 | 51.0 | 8.0 | 10.4 |
| 214 S | double | H | C(=O)N(CH$_3$)SN(CH$_3$)C$_6$H$_5$ | 91–93 | 53.7 | 5.1 | 12.5 | 53.6 | 5.0 | 12.1 |
| 220 S | double | 4-C(=O)OCH$_3$ | C(=O)NHCH$_3$ | oil | 46.9 | 4.7 | 10.9 | 46.6 | 5.0 | 10.5 |
| 221 S | double | 1-C(=O)OCH$_3$ | C(=O)NHCH$_3$ | 102–106 | 46.9 | 4.7 | 10.9 | 46.7 | 4.6 | 10.8 |
| 227 S | single | H | C(=O)N(CH$_3$)SC$_6$H$_4$C(CH$_3$)$_3$—4 | 121.5–125 | 59.3 | 6.6 | 7.7 | 59.5 | 6.6 | 7.7 |
| 228 S | double | H | C(=O)N(CH$_3$)SN(C$_8$H$_{17}$n)SO$_2$C$_6$H$_4$CH$_3$—4 | oil | 54.0 | 6.5 | 8.2 | 54.2 | 6.7 | 8.1 |
| 273 NH | double | H | C(=O)NHCH$_3$ | 98–100 | 53.0 | 6.1 | 23.2 | 53.1 | 6.2 | 23.2 |

TABLE II

[Structure: bicyclic skeleton with positions 1, 4, 5, 6, 7, 8, R substituent, =NOY group, and A]

| EX. NO. | A | a | R | Y | MELTING RANGE °C. | CALCULATED C | CALCULATED H | CALCULATED N | FOUND C | FOUND H | FOUND N |
|---|---|---|---|---|---|---|---|---|---|---|---|
| 33 | S | double | H | C(=O)NHCH₃ | 112-114 | 50.9 | 5.7 | 13.2 | 50.6 | 6.1 | 12.8 |
| 35 | S | double | 5(6)-CH₃—7-(8)CH(CH₃)₂— | C(=O)NHCH₃ | oil | 58.2 | 7.5 | 10.9 | 58.3 | 7.8 | 10.2 |
| 36 | S | single | H | C(=O)NHCH₃ | 115-116.5 | 50.4 | 6.6 | 13.1 | 50.4 | 6.7 | 12.4 |
| 37 | S | double | H | C(=O)NHCH₃ | 122-124 | 50.9 | 5.7 | 13.2 | 50.7 | 5.6 | 12.6 |
| 38 | S | double | 7,8-CH₂— | C(=O)NHCH₃ | 124.5-125.5 | 53.6 | 5.4 | 12.5 | 53.3 | 5.8 | 12.3 |
| 39 | S | single | 7,8-CH₂— | C(=O)NHCH₃ | 124-125 | 53.1 | 6.2 | 12.4 | 52.9 | 6.4 | 12.3 |
| 40 | S | double | 5(6)-(CH₂—CH₂)₂P(=O) | C(=O)NHCH₃ | oil | 42.8 | 5.8 | 7.7 | 43.0 | 6.3 | 7.6 |
| 41 | S | double | 4-CN | C(=O)NHCH₃ | 153-157 | 50.6 | 4.7 | 17.7 | 50.2 | 4.7 | 17.5 |
| 42 | S | double | H | C(=O)NHCH₂CH₃ | 92-94 | 53.1 | 6.2 | 12.4 | 53.0 | 6.3 | 12.1 |
| 43 | S | double | H | C(=O)NHCH₂CH₃ | 94-95 | 53.1 | 6.2 | 12.4 | 52.9 | 6.3 | 12.2 |
| 44 | S | double | 7(8)-C(=O)OCH₃ | H | oil | 50.7 | 5.2 | 6.6 | 50.1 | 5.5 | 6.2 |
| 45 | S | double | 1(4)C(=O)OCH₃ | H | 178-180 | 50.7 | 5.2 | 6.6 | 50.5 | 5.2 | 6.5 |
| 46 | S | double | 7(8)C(=O)OCH₃ | C(=O)NHCH₃ | 139-142 | 48.9 | 5.2 | 10.4 | 48.8 | 5.3 | 10.3 |
| 47 | S | double | 4(1)C(=O)OCH₃ | C(=O)NHCH₃ | 122-125 | 48.9 | 5.2 | 10.4 | 48.5 | 5.3 | 10.4 |
| 48 | S | double | 4-CN | C(=O)NHCH₃ | 196-199 | 53.3 | 4.5 | 15.5 | 53.1 | 4.7 | 15.3 |
| 49 | S | single | H | C(=O)N(CH₃)S—N(CH₃)C(=O)OCH₂CH₃ | 77-78.5 | 44.9 | 6.1 | 12.1 | 44.8 | 6.3 | 11.8 |
| 50 | S | double | H | C(=O)N(CH₃)S—N(CH₃)C(=O)O(CH₂)₃CH₃ | 94.5-95 | 48.2 | 6.2 | 11.2 | 48.0 | 6.5 | 11.2 |
| 51 | S | double | H | C(=O)N(CH₃)S—N(CH₃)C(=O)OC₆H₄—C(CH₃)₃—4 | 140-140.5 | 60.3 | 6.9 | 7.4 | 59.7 | 7.1 | 7.5 |
| 52 | S | double | H | C(=O)N(CH₃)S—C₆H₄-C(CH₃)₃—4 | 104-104.5 | 44.6 | 6.1 | 11.1 | 44.5 | 6.4 | 11.0 |
| 53 | S | double | H | C(=O)N(CH₃)S—N(CH₃)C(=O)OCH₂—CH₂OCH₃ | 123-125 | 50.7 | 5.7 | 9.9 | 50.6 | 5.9 | 9.9 |
| 54 | S | single | H | C(=O)NHCH₃ | 132-134 | 52.8 | 5.8 | 6.2 | 52.8 | 6.0 | 6.1 |
| 55 | S | double | 1(4)-C(=O)O—CH₂CH₃ | H | oil | 50.7 | 5.7 | 9.8 | 50.7 | 6.0 | 9.3 |
| 56 | S | single | 1(4)C(=O)—OCH₂CH₃ | C(=O)N(CH₃)S—N(CH₃)C(=O)OCH(CH₃)₂ | 93-95 | 46.5 | 6.4 | 11.6 | 46.7 | 6.5 | 11.6 |
| 57 | S | double | 1(4)C(=O)—OCH₂CH₃ | C(=O)N(CH₃)S—N(CH₃)C(=O)OQ | 190 | 47.6 | 4.9 | 12.3 | 47.8 | 5.0 | 12.2 |
| 59 | S | single | H | C(=O)NHCH₂CH₃ | 82-83 | 52.6 | 7.4 | 12.2 | 52.6 | 7.4 | 12.1 |
| 60 | S | single | H | C(=O)N(CH₃)S—NCH₂CH₂OCH₂CH₂ | 95-96 | 46.8 | 6.7 | 12.5 | 47.1 | 6.4 | 12.7 |
| 61 | S | double | 5(6)-Br | C(=O)NHCH₃ | oil | 37.1 | 3.8 | 9.6 | 37.5 | 4.2 | 9.5 |
| 62 | S | double | 5(6)-Br | C(=O)NHCH₃ | 87-89 | 37.1 | 3.8 | 9.6 | 37.0 | 4.0 | 7.5 |
| 63 | S | double | 5(6)-Br | H | 142-145 | 35.9 | 3.4 | 6.0 | 36.2 | 3.5 | 6.0 |
| 64 | S | double | 5(6)-Br | H | 126-128 | 35.9 | 3.4 | 6.0 | 36.0 | 3.6 | 5.9 |
| 65 | S | single | H | C(=O)N(CH₃)S—N(CH₃)C(=O)OCH₃ | 96-99 | 43.2 | 5.7 | 12.6 | 43.1 | 6.0 | 12.4 |
| 66 | S | single | H | C(=O)N(CH₃)SNC₅H₁₀ | oil | 51.0 | 7.0 | 12.7 | 51.2 | 7.2 | 12.4 |
| 67 | S | single | H | C(=O)N(CH₃)S(=O)—C₆H₄C—(CH₃)₃—4 | 156-158 | 57.8 | 6.6 | 7.1 | 57.8 | 6.9 | 6.9 |
| 68 | S | single | H | C(=O)N(CH₃)S—C₆H₄C(CH₃)₃—4·H₂O | 119-120 | 57.8 | 6.6 | 7.1 | 57.9 | 6.3 | 7.1 |
| 69 | S | double | 7,8-CH(CN)— | C(=O)NHCH₃ | 125 | 53.0 | 4.4 | 16.9 | 53.1 | 4.5 | 16.2 |
| 71 | S | double | 5-(6)-Cl | C(=O)N(CH₃)S—C₆H₄C(CH₃)₃—4 | 122-123 | 60.6 | 6.4 | 7.4 | 60.3 | 6.7 | 7.3 |
| 72 | S | double | H | H | oil | 43.8 | 4.5 | 11.3 | 43.7 | 4.5 | 11.1 |
| 73 | S | double | 5(6)Cl | C(=O)NHCH₃ | 116-119 | 44.3 | 4.2 | 11.3 | 44.1 | 4.2 | 11.3 |
| 74 | S | double | 5(6)Cl | C(=O)NHCH₃ | 61-64 | 43.8 | 4.5 | 11.3 | 43.5 | 4.7 | 11.3 |
| 75 | S | double | 5(6)Cl | C(=O)NHCH₃ | 101-104 | 43.8 | 4.5 | 11.3 | 43.7 | 4.6 | 11.3 |

TABLE II-continued

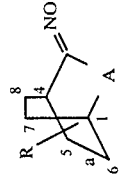

| EX. NO. | A | a | R | Y | MELTING RANGE °C. | CALCULATED C | CALCULATED H | CALCULATED N | FOUND C | FOUND H | FOUND N |
|---|---|---|---|---|---|---|---|---|---|---|---|
| 76 | S | double | 5(6)Cl | H | 110-113 | 44.3 | 4.2 | 7.4 | 44.0 | 4.5 | 7.1 |
| 77 | S | single | H | C(=O)N(CH₃)S—N(CH₃)SO₂N(CH₃)₂ | oil | 37.7 | 5.8 | 14.6 | 37.1 | 6.1 | 14.8 |
| 79 | S | single | H | C(=O)N(CH₃)S—C₆H₅ | 97-98 | 55.9 | 5.6 | 8.7 | 55.8 | 6.0 | 8.6 |
| 80 | S | double | H | C(=O)N(CH₃)SC₆H₅ | 112-113 | 56.2 | 5.0 | 8.7 | 56.4 | 4.8 | 8.7 |
| 82 | S | double | 4-CN | C(=O)N(CH₃)SC₆H₅ | 139-141 | 55.6 | 4.4 | 12.2 | 55.5 | 4.3 | 12.2 |
| 83 | S | double | H | C(=O)N(CH₃)S—NCH₂CH₂OCH₂CH₂ | 112-113 | 47.4 | 5.8 | 12.7 | 47.4 | 6.0 | 12.7 |
| 88 | S | double | 4-CN | C(=O)N(CH₃)SN(CH₃)C(=O)Q | 198-199 | 47.6 | 4.0 | 16.7 | 47.5 | 4.0 | 16.2 |
| 90 | S | double | H | C(=O)N(CH₃)S—N(CH₃)SO₂N(CH₃)₂ | 125-126 | 37.9 | 5.3 | 14.7 | 37.7 | 5.5 | 14.7 |
| 91 | S | single | H | C(=O)N(CH₃)S—(2-CH₃—4-(CH₃)₃C)C₆H₃ | 125-126 | 61.2 | 7.2 | 7.1 | 60.9 | 7.4 | 7.2 |
| 92 | S | double | 4-CN | C(=O)N(CH₃)S—(2-CH₃—4-(CH₃)₃C)C₆H₃ | 189-190 | 60.7 | 6.1 | 10.1 | 60.6 | 6.3 | 10.0 |
| 94 | S | single | 4-CN | C(=O)N(CH₃)SO₂C₆H₄CH₃—4 | 222-225 | 52.7 | 5.5 | 15.4 | 52.7 | 5.6 | 15.3 |
| 95 | S | single | 4-CN | C(=O)N(CH₃)S—C₆H₄CH₃—3 | 178-180 | 50.2 | 4.2 | 17.6 | 49.8 | 5.4 | 17.5 |
| 96 | S | double | 4-Cl | C(=O)NHCH₃ | 185-188 | 44.3 | 4.5 | 7.4 | 44.4 | 4.4 | 7.1 |
| 97 | S | double | 4-Cl | H | 104-106 | 43.8 | 4.5 | 11.3 | 43.9 | 4.6 | 11.1 |
| 98 | S | single | H | C(=O)NHCH₃ | 118-119 | 57.1 | 6.0 | 8.3 | 57.3 | 6.0 | 8.4 |
| 99 | S | double | H | C(=O)N(CH₃)S—C₆H₄—CH₃—2 | 120-121 | 57.5 | 5.4 | 8.4 | 57.2 | 5.7 | 8.3 |
| 100 | S | single | H | C(=O)N(CH₃)S—C₆H₄—CH₃—2 | 119-120 | 54.5 | 5.7 | 7.9 | 54.5 | 6.0 | 8.0 |
| 102 | S | single | H | C(=O)N(CH₃)S—C₆H₄—(OCH₃)—4 | 154-156 | 47.5 | 5.4 | 9.8 | 47.2 | 5.6 | 9.5 |
| 103 | S | double | 4-CN | C(=O)N(CH₃)SN(CH₃)SO₂C₆H₄CH₃—4 | 158-159 | 56.8 | 4.8 | 11.7 | 56.4 | 4.7 | 11.6 |
| 104 | S | single | H | C(=O)N(CH₃)S—C₆H₄CF₃—3 | 93-94 | 49.5 | 3.9 | 7.2 | 50.0 | 4.2 | 7.2 |
| 105 | S | double | 4-CN | C(=O)N(CH₃)S—C₆H₄CF₃—3 | 148-149 | 49.4 | 3.4 | 10.2 | 49.6 | 3.6 | 10.2 |
| 106 | S | double | H | C(=O)N(CH₃)S—C₆H₄CH₃—3 | 77-78 | 57.5 | 5.4 | 8.4 | 57.1 | 5.5 | 8.2 |
| 107 | S | double | 4-CN | C(=O)N(CH₃)SC₆H₄(OCH₃)—4 | 77-78 | 54.4 | 5.4 | 7.9 | 54.8 | 5.2 | 8.0 |
| 108 | S | double | 4-CN | C(=O)N(CH₃)SN(CH₃)SO₂C₆H₄CH₃—4 | 180-182 | 47.8 | 4.4 | 12.4 | 47.9 | 4.6 | 12.5 |
| 109 | S | double | H | C(=O)N(CH₃)SC(CH₂)₂CN | 125.5-127 | 45.5 | 5.0 | 12.2 | 45.5 | 5.2 | 12.1 |
| 110 | S | single | H | C(=O)N(CH₃)SC₆H₄Cl—4 | 110-111 | 50.5 | 4.8 | 7.8 | 50.3 | 5.0 | 7.9 |
| 111 | S | double | H | C(=O)N(CH₃)SC₆H₄Cl—4 | 108-109 | 50.8 | 4.3 | 7.9 | 50.8 | 4.4 | 7.8 |
| 113 | S | double | 4-CN | C(=O)N(CH₃)SC₆H₄Cl—4 | 156-158 | 50.6 | 3.7 | 11.1 | 50.4 | 3.8 | 11.1 |
| 114 | S | double | 4-CN | C(=O)N(CH₃)SN(CH₃CH₂)SO₂C₆H₄CH₃—4 | 142-149 | 50.0 | 5.0 | 11.7 | 49.6 | 5.1 | 11.6 |
| 115 | S | single | H | C(=O)N(CH₃)SN(CH₂CH₃)SO₂C₆H₄CH₃—4 | 110-115 | 50.1 | 5.5 | 9.2 | 49.6 | 5.7 | 9.2 |
| 116 | S | double | 4-CN | C(=O)N(CH₃)SC₆H₄CH₃—4 | 122-124 | 56.8 | 4.8 | 11.7 | 56.7 | 5.0 | 11.9 |
| 118 | S | single | H | C(=O)N(CH₃)SC₆H₄CH₃—4 | 74-75 | 57.1 | 5.8 | 8.3 | 57.0 | 6.3 | 8.3 |
| 119 | S | double | H | C(=O)N(CH₃)SC₆H₄—NO₂—2 | 167-168 | 49.0 | 4.7 | 11.4 | 49.1 | 5.0 | 11.3 |
| 120 | S | double | H | C(=O)N(CH₃)SN(C₄H₉—n)SO₂C₆H₄—CH₃—4 | 107-108.5 | 51.1 | 5.8 | 9.0 | 50.9 | 6.0 | 9.0 |
| 121 | S | double | 4-CN | C(=O)N(CH₃)SN(C₄H₉—n)SO₂C₆H₄—CH₃—4 | 149.5-150.5 | 51.0 | 5.3 | 11.3 | 50.6 | 5.5 | 11.2 |
| 123 | S | double | H | C(=O)NHSSN(CH₃)C(=O)Q | 194-195 | 44.4 | 4.6 | 11.5 | 44.3 | 4.6 | 11.2 |
| 124 | S | single | H | C(=O)NHCH₂CH₃ | 184 | 55.0 | 6.7 | 11.4 | 54.7 | 7.1 | 11.3 |
| 127 | S | double | H | C(=O)N(CH₃)SC₆H₄CH₃ | 84-85 | 49.0 | 5.8 | 8.3 | 49.1 | 6.3 | 11.5 |
| 132 | S | single | H | C(=O)N(CH₃)SC₆H₄Br—4 | 137-138 | 44.9 | 4.3 | 7.0 | 44.8 | 4.3 | 6.9 |
| 133 | S | double | H | C(=O)N(CH₃)SC₆H₄Br—4 | 128-129 | 45.1 | 3.8 | 7.0 | 45.0 | 3.8 | 7.0 |

TABLE II-continued

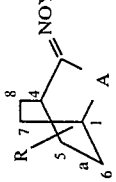

| EX. NO. | A | a | R | Y | MELTING RANGE °C. | CALCULATED C | CALCULATED H | CALCULATED N | FOUND C | FOUND H | FOUND N |
|---|---|---|---|---|---|---|---|---|---|---|---|
| 134 | S | single | H | H | 150-152.5 | 53.5 | 7.1 | 8.9 | 53.4 | 7.2 | 9.1 |
| 136 | S | double | 4-CN | C(=O)N(CH₃)SC₆H₅—Cl—2 | 166-167 | 50.6 | 3.7 | 11.1 | 50.6 | 3.7 | 11.2 |
| 140 | S | double | H | C(=O)N(CH₃)SN(CH(CH₃)₂)SO₂C₆H₄—CH₃—4 | 181-181.5 | 50.1 | 5.5 | 9.2 | 50.0 | 5.8 | 9.1 |
| 141 | S | double | 4-CN | C(=O)N(CH₃)SN(CH(CH₃)₂)SO₂C₆H₄—CH₃—4 | 202-203 | 50.0 | 5.0 | 11.7 | 49.9 | 5.3 | 11.8 |
| 142 | S | single | H | C(=O)N(CH₃)SC₆H₄Cl—2 | 116-118 | 50.5 | 4.8 | 7.8 | 50.6 | 4.9 | 7.8 |
| 145 | S | double | H | C(=O)N(CH₃)SN(CH₃)C(=O)OCH₃ | 120-122 | 43.5 | 5.2 | 12.7 | 43.5 | 5.4 | 12.4 |
| 150 | S | double | 4-CN | C(=O)N(CH₃)SN(CH₂CH₃)SO₂C₆H₅ | 122-123 | 48.9 | 4.7 | 12.0 | 48.6 | 4.9 | 12.2 |
| 151 | S | double | H | C(=O)N(CH₃)SN(CH₂CH₃)SO₂C₆H₅ | 92-96 | 49.0 | 5.2 | 9.5 | 49.3 | 5.5 | 9.6 |
| 155 | S | single | H | C(=O)N(CH₃)SC₆H₃(NO₂)₂—2,4 | 206-208 | 43.7 | 3.9 | 13.6 | 43.5 | 3.9 | 13.6 |
| 156 | S | double | H | C(=O)NHCH₂CH=CH₂ | 90-91 | 55.4 | 5.9 | 11.8 | 55.0 | 6.1 | 11.8 |
| 158 | S | single | H | C(=O)N(CH₃)SN(C₄H₉—n)SO₂C₆H₄—CH₃—4 | 123.5-126.5 | 50.9 | 6.2 | 8.9 | 50.9 | 6.4 | 9.0 |
| 159 | S | single | H | C(=O)N(CH₃)SC₆H₄F—4 | 66-67 | 52.9 | 5.0 | 8.2 | 52.8 | 5.3 | 8.3 |
| 162 | S | single | H | C(=O)N(CH₃)SN(CH₂CH₂CH₃)SO₂C₆H₅ | 128-131 | 48.7 | 5.7 | 9.5 | 48.7 | 5.7 | 9.7 |
| 163 | S | double | 4-CN | C(=O)N(CH₃)SN(CH₂CH₂CH₃)SO₂CH₃ | 115-117.5 | 41.1 | 5.6 | 11.1 | 40.8 | 5.9 | 11.0 |
| 165 | S | double | 4-CN | C(=O)N(CH₃)SN(CH₂CH₂CH₃)SO₂C₆H₄—Cl—4 | 155-156.5 | 45.5 | 4.2 | 10.7 | 45.5 | 4.2 | 11.2 |
| 166 | S | double | H | C(=O)N(CH₃)S—N(CH₂CH₂CH₃)SO₂—C₆H₄Cl—4 | 142-143.5 | 45.4 | 4.7 | 8.8 | 45.3 | 4.7 | 8.9 |
| 168 | S | double | 4-CN | C(=O)NHCH₂CH=CH₂ | 83-85 | 54.7 | 5.0 | 16.0 | 54.4 | 5.2 | 15.9 |
| 169 | S | double | 4-CN | C(=O)N(CH₃)SN(CH₂CH₂CH₃)SO₂CH₃ | 119.5-121.5 | 40.9 | 6.1 | 11.0 | 41.2 | 6.4 | 11.0 |
| 171 | S | double | 4-CN | C(=O)N(CH₃)SN(CH₂CH₂CH₃)SO₂CH₃ | 155-156.5 | 41.6 | 5.3 | 13.8 | 41.4 | 5.3 | 13.8 |
| 173 | S | double | H | C(=O)N(CH₃)SN(CH₃)C(=O)OCH₃ | 79-80 | 46.8 | 5.9 | 11.7 | 46.2 | 6.1 | 11.6 |
| 176 | S | double | 4-CN | C(=O)N(CH₃)SC₆H₄F—4 | 112-115 | 52.9 | 3.9 | 11.6 | 53.1 | 4.0 | 11.3 |
| 177 | S | double | H | C(=O)N(CH₃)₂ | 118-119 | 53.1 | 6.2 | 12.4 | 52.8 | 6.5 | 12.2 |
| 179 | S | single | H | C(=O)N(CH₃)SN(CH(CH₃)₂)SO₂N(CH₃)₂ | 90-92 | 40.9 | 6.4 | 13.6 | 41.0 | 6.7 | 13.5 |
| 180 | S | double | 4-CN | C(=O)N(CH₃)₂ | 174-176 | 52.6 | 5.2 | 16.7 | 52.2 | 5.4 | 16.6 |
| 181 | S | single | H | C(=O)N(CH₃)SC₆H₄CN—2 | 137-138 | 55.3 | 4.9 | 12.1 | 55.5 | 5.1 | 12.2 |
| 184 | S | double | H | C(=O)N(CH₃)S—N(C₆H₅)C(=O)OCH₃ | 120-121 | 51.9 | 4.9 | 10.7 | 51.6 | 5.1 | 10.5 |
| 186 | S | single | H | C(=O)N(CH₃)SN(CH₃)C(=O)ON—(-2-CH₃—2,5-(—C(CH₃)₂—)C₆H₇) | 160-161.5 | 53.8 | 6.9 | 12.0 | 53.6 | 7.4 | 11.7 |
| 188 | S | double | H | C(=O)N(CH₃)S—N(CH(CH₃)₂)SO₂N(CH₃)₂ | 126-128 | 41.1 | 5.9 | 13.7 | 41.3 | 6.2 | 13.8 |
| 189 | S | double | 4-CN | C(=O)N(CH₃)SN(CH₃)C(=O)OCH₃ | 130-131 | 43.8 | 4.5 | 15.7 | 43.8 | 5.1 | 15.4 |
| 190 | S | double | 4-CN | C(=O)N(CH₃)S—C₆H₄(OCH₃)—2 | 163-164 | 54.4 | 4.6 | 11.2 | 54.2 | 4.5 | 11.3 |
| 192 | S | single | H | C(=O)N(CH₃)C(=O)OCH₃)—2 | foam | 57.0 | 5.0 | 10.6 | 57.0 | 5.0 | 10.3 |
| 193 | S | single | 5,6-(CH₃O)₂ | C(=O)NHCH₃ | 156-157 | 48.2 | 6.6 | 10.2 | 48.0 | 6.9 | 10.4 |
| 194 | S | single | H | C(=O)N(CH₃)SSCH₂CH₂CH₃ | semi solid | 46.7 | 6.6 | 8.4 | 46.4 | 6.7 | 8.2 |
| 195 | S | single | H | C(=O)N(CH₃)SN(CH₃)C(=O)OCH₂C₆H₄—(OC₆H₅)—3 | glass | 56.6 | 5.4 | 8.2 | 56.0 | 5.5 | 8.2 |
| 196 | O | double | H | C(=O)NHCH₃ | 103-104 | 55.1 | 6.2 | 14.3 | 54.8 | 6.5 | 14.3 |
| 197 | S | single | H | C(=O)N(CH₃)SC₆H₄(OCH₃)—2 | 134-135 | 54.5 | 5.7 | 7.9 | 54.2 | 6.0 | 8.0 |
| 198 | S | single | H | C(=O)N(CH₃)SNCH₂CH₂SCH₂CH₂ | 110-111 | 44.9 | 6.1 | 12.1 | 44.9 | 6.4 | 12.2 |
| 199 | S | double | H | C(=O)N(CH₃)CH₃)CH₂OH | 107-112 | 49.6 | 5.8 | 11.6 | 49.6 | 5.9 | 11.6 |
| 200 | S | double | 4-CN | C(=O)NH₂ | 193-194 | 48.4 | 4.1 | 18.8 | 48.3 | 4.0 | 18.4 |
| 201 | S | double | 4-CN | C(=O)NHCH₂CH₃ | 104.5-105.5 | 52.6 | 5.2 | 16.7 | 52.7 | 5.2 | 16.9 |

TABLE II-continued

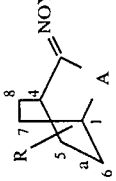

| EX. NO. | A | a | R | Y | MELTING RANGE °C. | CALCULATED C | CALCULATED H | CALCULATED N | FOUND C | FOUND H | FOUND N |
|---|---|---|---|---|---|---|---|---|---|---|---|
| 202 | S | double | 4-CN | C(=O)NHCH$_2$CH$_3$ | 50.5-53.0 | 54.3 | 5.7 | 15.8 | 54.2 | 5.8 | 15.7 |
| 203 | S | single | H | C(=O)N(CH$_3$)SN(CH$_3$)C$_6$H$_5$ | 115-116 | 54.6 | 6.0 | 12.0 | 54.8 | 6.1 | 11.9 |
| 204 | S | single | H | C(=O)N(CH$_3$)SN(CH$_3$)C(=O)NHC$_6$H$_5$ | 67.5 | 51.2 | 5.6 | 14.0 | 51.1 | 5.7 | 14.0 |
| 205 | S | double | 4-CN | C(=O)NHCH(CH$_3$)$_2$ | 112-113.5 | 54.3 | 5.7 | 15.8 | 54.8 | 5.8 | 15.9 |
| 206 | S | double | 4-CN | C(=O)N(CH$_3$)CH$_2$OH | 124-126 | 49.4 | 4.9 | 15.7 | 49.0 | 4.7 | 15.9 |
| 207 | O | double | H | C(=O)N(CH$_3$)SC$_6$H$_4$C(CH$_3$)$_3$-4 | 129-130 | 63.3 | 6.7 | 7.8 | 63.1 | 6.7 | 8.1 |
| 208 | S | single | H | C(=O)N(CH$_3$)SN(C$_{12}$H$_{25}$n)SO$_2$N(CH$_3$)$_2$ | 92-93 | 51.4 | 8.3 | 10.4 | 61.3 | 8.4 | 10.6 |
| 210 | O | double | H | C(=O)N(CH$_3$)SN(CH$_3$)C(=O)OQ | 176 | 51.2 | 5.2 | 13.3 | 51.2 | 5.4 | 12.9 |
| 211 | O | single | H | C(=O)NHCH$_3$ | 111-112 | 54.5 | 7.1 | 14.1 | 54.8 | 7.4 | 14.3 |
| 213 | S | double | H | C(=O)N(CH$_3$)SN(C$_{12}$H$_{25}$n)SO$_2$N(CH$_3$)$_2$ | 76-78 | 51.6 | 7.9 | 10.5 | 51.7 | 8.1 | 10.3 |
| 215 | S | double | 4-CN | C(=O)N(CH$_3$)SN(C$_{12}$H$_{25}$n)SO$_2$N(CH$_3$)$_2$ | 116-117 | 51.5 | 7.4 | 12.5 | 51.2 | 7.6 | 12.5 |
| 216 | S | double | H | C(=O)N(CH$_3$)CH$_2$OC(=O)CH$_3$ | oil | 50.7 | 5.7 | 9.8 | 50.7 | 5.9 | 9.7 |
| 217 | S | double | 4-CN | C(=O)N(CH$_3$)SN(CH$_3$)C$_6$H$_5$ | 133-134 | 54.5 | 4.8 | 15.0 | 54.7 | 4.7 | 15.0 |
| 218 | S | double | 4-CN | C(=O)N(CH$_3$)SN(CH$_3$)C(=O)ON=C(CH$_2$—SCH$_3$)C(CH$_3$)$_3$ | 57-64 | 48.3 | 5.5 | 14.1 | 47.6 | 5.8 | 14.6 |
| 219 | S | double | H | C(=O)N(CH$_3$)SN(C$_8$H$_{17}$n)SO$_2$C$_6$H$_4$—CH$_3$-4 | oil | 54.8 | 6.7 | 8.0 | 54.3 | 6.8 | 7.5 |
| 222 | S | double | 4-CN | C(=O)N(CH$_3$)SN(CH$_3$)C(=O)O(CH$_2$)$_{11}$CH$_3$ | 101-102.5 | 47.0 | 5.4 | 11.8 | 46.9 | 5.3 | 12.1 |
| 223 | O | single | H | C(=O)N(CH$_3$)SSCH$_2$CH$_2$CH$_3$ | 165-166 | 59.6 | 7.8 | 9.9 | 59.2 | 7.8 | 10.0 |
| 224 | S | double | H | H | 153-154 | 60.4 | 6.5 | 10.1 | 60.8 | 6.5 | 9.9 |
| 226 | S | double | H | H | 62-64 | 47.0 | 6.1 | 8.4 | 47.3 | 6.1 | 8.7 |
| 229 | S | double | 4-CN | C(=O)N(CH$_3$)SSCH$_2$CH$_2$CH$_3$ | 177-179.5 | 48.9 | 4.8 | 12.0 | 49.2 | 4.8 | 12.0 |
| 230 | S | double | 4-CN | C(=O)N(CH$_3$)SN(CH$_3$)$_2$)SO$_2$C$_6$H$_5$ | 133.5-135 | 54.5 | 6.2 | 10.2 | 54.5 | 6.3 | 10.0 |
| 233 | S | double | 4-CN | C(=O)N(CH$_3$)SN(C$_8$H$_{17}$—n)SO$_2$C$_6$H$_4$—CH$_3$-4 | 93-95 | 56.4 | 7.5 | 11.0 | 56.7 | 7.7 | 11.0 |
| 234 | O | double | H | C(=O)N(CH$_3$)SN(CH$_3$)C(=O)O(CH$_2$)$_{11}$CH$_3$ | 195 | 47.6 | 4.9 | 12.3 | 47.0 | 5.0 | 12.2 |
| 235 | S | double | H | C(=O)N(CH$_3$)S—SN(CH$_3$)C$_6$H$_4$CH$_3$-2 | 171-172 | 56.8 | 4.8 | 11.7 | 56.6 | 4.7 | 11.7 |
| 236 | S | single | H | C(=O)N(CH$_3$)SSC$_6$H$_5$ | oil | 50.8 | 5.1 | 7.9 | 51.2 | 5.2 | 7.4 |
| 237 | O | double | H | C(=O)N(CH$_3$)SN(C$_4$H$_9$—n)$_2$ | oil | 54.5 | 7.1 | 14.1 | 54.6 | 7.3 | 13.7 |
| 238 | S | double | 4-CN | C(=O)N(CH$_3$)SC(CH$_3$)$_2$C(=O)CH$_3$ | 128-129.5 | 51.0 | 5.4 | 11.9 | 50.7 | 5.4 | 12.0 |
| 239 | S | double | 4-CN | C(=O)N(CH$_3$)SN(C$_{12}$H$_{25}$—n)C(=O)N—(CH$_3$)$_2$ | 61.5-65 | 57.3 | 7.9 | 13.4 | 57.2 | 7.8 | 13.3 |
| 240 | S | double | 4-CN | C(=O)N(CH$_3$)SN(CH$_3$)CH$_2$C(=O)OCH$_2$—CH$_3$)SO$_2$C$_6$H$_4$CH$_3$-4 | 139.5-141.5 | 48.1 | 4.6 | 10.7 | 48.1 | 4.6 | 10.7 |
| 241 | S | double | 4-CN | C(=O)N(CH$_3$)SN(CH$_3$)SO$_2$C$_6$H$_4$—(OCH$_3$)-4 | 122-125 | 48.3 | 4.9 | 11.3 | 48.3 | 4.8 | 11.2 |
| 242 | S | double | 4-CN | C(=O)NH(CH$_2$)$_{11}$CH$_3$ | 59-60 | 64.4 | 8.5 | 10.7 | 64.6 | 8.8 | 10.8 |
| 243 | S | double | 4-Cl | C(=O)NHCH$_2$CH$_2$CH$_3$ | oil | 48.1 | 5.5 | 10.2 | 47.7 | 5.8 | 10.0 |
| 244 | S | double | 4-Cl | C(=O)N(CH$_3$)SC$_6$H$_4$C(CH$_3$)$_3$-4 | 137-139.5 | 55.5 | 5.6 | 6.8 | 55.0 | 5.8 | 6.8 |
| 245 | S | double | 4-CN | C(=O)N(CH$_3$)SN(CH$_3$)SO$_2$N(C$_4$H$_9$—n)$_2$ | 103-105 | 46.6 | 6.4 | 14.3 | 46.3 | 6.7 | 14.3 |
| 246 | S | double | 4-CN | C(=O)N(CH$_3$)SNCH$_2$CH$_2$SCH$_2$CH$_2$ | 138-139 | 45.4 | 4.9 | 15.1 | 45.5 | 5.1 | 15.2 |
| 247 | S | double | 4-CN | C(=O)N(CH$_3$)SC(=O)OC$_{12}$H$_{25}$—n | 74-76 | 57.4 | 7.3 | 8.7 | 57.1 | 7.6 | 8.8 |
| 248 | S | double | 4-CN | C(=O)N(CH$_3$)SN(CH$_2$CH$_2$CH$_3$)P(S)—(OCH$_2$CH$_3$)$_2$ | 89.5-91 | 42.7 | 5.7 | 11.7 | 42.6 | 6.1 | 11.9 |

TABLE II-continued

![Structure with R at position 7, 8 substituent =NOY, A at position 1, a bond between 5a and 6]

| EX. NO. | A | a | R | Y | MELTING RANGE °C. | CALCULATED C | CALCULATED H | CALCULATED N | FOUND C | FOUND H | FOUND N |
|---|---|---|---|---|---|---|---|---|---|---|---|
| 249 | S | double | 4-CN | C(=O)N(CH₃)SNCH₂CH₂SO₂CH₂CH₂ | 202–204 | 41.8 | 4.5 | 13.9 | 41.8 | 4.5 | 13.9 |
| 250 | S | double | 4-CN | C(=O)NHC₄H₉—n | semi-solid | 55.8 | 6.1 | 15.0 | 55.8 | 6.3 | 15.2 |
| 251 | S | double | 4-CN | C(=O)NHC₄H₉—tert | 150–151 | 55.8 | 6.1 | 15.0 | 56.3 | 6.4 | 15.0 |
| 252 | S | double | 4-CN | C(=O)N(CH₃)SN(CH₃)C(=O)O—CH₂—(C₄H₃O)—2 | 136.5–138 | 48.3 | 4.3 | 13.3 | 48.2 | 4.3 | 13.2 |
| 253 | S | double | 4-Cl | C(=O)N(CH₃)SN(C₁₂H₂₅—n)C(=O)N—(CH₃)₂ | 77–78.5 | 54.1 | 7.8 | 10.5 | 53.9 | 7.8 | 10.5 |
| 254 | S | double | 4-CN | C(=O)N(CH₃)S—N(C₆H₅)SO₂N(CH₃)₂ | 178.5–180 | 46.2 | 4.5 | 15.0 | 46.4 | 4.5 | 15.0 |
| 255 | S | double | 4-CN | C(=O)N(CH₃)SSC₆H₅ | oil | 50.9 | 4.0 | 11.1 | 50.7 | 4.2 | 10.9 |
| 256 | S | double | 4-CN | C(=O)N(CH₃)SSC₆H₄C(CH₃)₃—4 | 118–120 | 55.4 | 5.4 | 9.7 | 55.4 | 5.3 | 9.6 |
| 257 | S | double | 4-CN | C(=O)N(CH₃)SC₆H₄(OCH₃)—4 | 122–123 | 54.4 | 4.6 | 11.2 | 54.1 | 4.6 | 11.2 |
| 258 | S | double | 4-CN | C(=O)N(CH₃)SC₈H₁₇—n | 89–91 | 55.6 | 7.4 | 13.6 | 55.7 | 7.3 | 13.6 |
| 259 | S | double | 4-CN | C(=O)N(CH₃)SN(CH₂CH₃)SO₂CH₂C₆H₅ | 154–156 | 50.0 | 5.0 | 11.7 | 50.1 | 5.0 | 11.7 |
| 260 | S | double | 4-CN | C(=O)NHCH₂CH(CH₃)₂ | 85–87 | 55.8 | 6.1 | 15.0 | 55.6 | 6.3 | 15.0 |
| 261 | S | double | 4-CN | C(=O)N(CH₃)SN(CH₃)C(=O)NHCH₃ | 136–137 | 43.9 | 4.8 | 19.7 | 44.0 | 4.9 | 19.7 |
| 262 | S | double | 4-CN | C(=O)N(CH₃)SN(CH₂CH₃)—P(S)OCH₂C(CH₃)₂CH₂O | 129–130 | 44.1 | 5.6 | 11.4 | 43.9 | 5.7 | 11.5 |
| 263 | S | double | 4-CN | C(=O)N(CH₃)SN(CH₃)C(=O)C₆H₄C₄H₉—4 | 69–75 | 59.5 | 6.7 | 10.3 | 59.5 | 6.8 | 10.2 |
| 264 | S | double | 4-CN | C(=O)N(CH₃)SN(CH₃)C(=O)OCH₂CH₂OCH₃ | 110–112 | 45.0 | 5.0 | 14.0 | 45.2 | 5.0 | 14.0 |
| 265 | S | double | 4-CN | C(=O)N(CH₃)S—C₆H₁₁Cl—2 | 51 | 49.8 | 5.2 | 10.9 | 49.8 | 5.4 | 10.7 |
| 266 | S | double | 4-CN | C(=O)N(CH₃)SN(C₁₂H₂₅—n)SO₂NC₄H₈ | 121–123 | 53.3 | 7.4 | 12.0 | 53.1 | 7.2 | 11.8 |
| 267 | S | double | 4-CN | C(=O)N(CH₃)SSC₆H₄—Cl—2 | 105–107 | 46.6 | 3.4 | 10.2 | 47.6 | 3.6 | 10.0 |
| 268 | S | double | 4-CN | C(=O)N(CH₃)SN(CH₃)C(=O)N(C₄H₉—n)₂ | 85–86 | 53.0 | 6.9 | 15.4 | 52.8 | 7.0 | 15.5 |
| 270 | NH | double | 4-CN | C(=O)NHCH₃ | 128–129 | 55.4 | 6.7 | 21.5 | 55.6 | 6.9 | 21.6 |
| 271 | S | double | H | C(=O)N(CH₃)SC₁₂H₂₅ | oil | 60.4 | 8.1 | 9.6 | 60.1 | 8.3 | 8.9 |
| 272 | S | double | 4-CN | C(=O)N(CH₃)SNCH₂CH₂OCH₂CH₂ | 59–63 | 47.4 | 5.1 | 15.8 | 47.1 | 4.9 | 15.5 |
| 274 | S | double | 4-CN | C(=O)NHCH₂OCH₃ | 109.5–111.5 | 49.4 | 4.9 | 15.7 | 49.3 | 4.9 | 15.7 |
| 275 | S | double | H | C(=O)N(CH₃)SSC(CH₃)₃ | 99.5–103 | 47.0 | 6.1 | 8.4 | 46.9 | 6.4 | 8.5 |
| 276 | S | double | 4-CN | C(=O)N(CH₃)SN(CH₂CH₃)SO₂—(C₅H₄N)—3 | 87–90 | 46.2 | 4.5 | 15.0 | 46.4 | 4.6 | 14.6 |
| 277 | S | double | 4-CN | C(=O)NHC₈H₁₇—n | 47–49 | 60.9 | 7.5 | 12.5 | 60.8 | 7.9 | 12.6 |
| 278 | S | double | H | C(=O)N(CH₃)SN(CH₂CH₃)SO₂—(C₅H₄N)—3 | 94–98 | 46.1 | 5.0 | 12.7 | 45.9 | 5.1 | 12.6 |
| 279 | S | double | H | C(=O)N(CH₃)SSC₁₂H₂₅—n | 36–38 | 56.7 | 8.2 | 6.3 | 56.8 | 8.4 | 6.6 |
| 280 | SO₂ | double | 4-CN | C(=O)NHCH₃ | 196–198 | 44.6 | 4.1 | 15.6 | 44.3 | 4.1 | 15.3 |
| 281 | S | double | 4-CN | C(=O)NHCH₂C₆H₅ | 105–106 | 61.3 | 4.8 | 13.4 | 61.2 | 4.9 | 13.3 |
| 282 | S | double | 4-CN | C(=O)NHCH₂(CH₂CH₂O)₃CH₂CH₃ | oil | 54.4 | 6.8 | 10.6 | 54.0 | 6.9 | 11.0 |
| 286 | S | double | H | C(=O)N(CH₃)SSC₆H₄C(CH₃)—4 | 83–85 | 55.8 | 5.9 | 6.9 | 56.1 | 6.0 | 7.1 |

TABLE II-continued
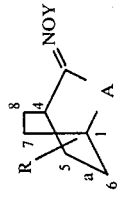
| EX. NO. | A | a | R | Y | MELTING RANGE °C. | CALCULATED C | CALCULATED H | CALCULATED N | FOUND C | FOUND H | FOUND N |
|---|---|---|---|---|---|---|---|---|---|---|---|
| 287 | O | single | H | C(=O)NHC$_{12}$H$_{25}$—n | 69–72 | 68.1 | 10.3 | 8.0 | 67.9 | 10.3 | 8.0 |
| 288 | S | double | 4-CN | C(=O)NHC$_{16}$H$_{33}$—n | 71–73 | 67.1 | 9.2 | 9.4 | 67.3 | 9.2 | 9.2 |
| 289 | S(O) | double | 4-CN | C(=O)NHCH$_3$ | 178–179 | 47.4 | 4.4 | 16.6 | 47.1 | 4.3 | 16.3 |
| 290 | S | double | 1-CH$_3$—4-CN— | C(=O)NHCH$_3$ | 138–140 | 52.6 | 5.2 | 16.7 | 53.1 | 5.3 | 16.8 |
| 291 | S | double | 1-CH$_3$—4-CN | H | 200.5–201.5 | 56.2 | 6.2 | 14.4 | 55.8 | 5.3 | 14.4 |
| 292 | NCH$_3$ | single | H | C(=O)NHCH$_3$ | oil | 56.8 | 8.1 | 19.9 | 55.5 | 8.2 | 19.4 |
| 293 | S | double | H | C(=O)NHC$_{12}$H$_{25}$—n | 52–54 | 65.5 | 9.4 | 7.6 | 65.6 | 9.4 | 7.6 |
| 294 | S | double | 4-CN—6-CH$_3$— | C(=O)NHCH$_3$ | 115–116.5 | 52.6 | 5.2 | 16.7 | 52.5 | 5.3 | 16.8 |

TABLE III

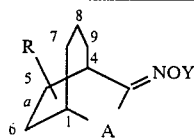

| EX. NO. | A | a | R | Y | MELTING RANGE °C. | CALCULATED C | H | N | FOUND C | H | N |
|---|---|---|---|---|---|---|---|---|---|---|---|
| 84 | S | double | H | C(=O)NHCH₃ | oil | 53.1 | 6.2 | 12.4 | 53.4 | 6.5 | 12.1 |
| 85 | S | double | H | C(=O)NHCH₂CH₃ | oil | 55.0 | 6.7 | 11.7 | 55.1 | 6.8 | 11.3 |
| 86 | S | single | H | C(=O)NHC(CH₃)₃ | 111-113 | 57.8 | 8.2 | 10.4 | 57.7 | 8.5 | 10.4 |
| 87 | S | double | H | C(=O)NHC(CH₃)₃ | 87-89 | 58.2 | 7.5 | 10.4 | 58.3 | 7.6 | 10.5 |
| 93 | S | single | H | C(=O)NHCH₃ | 112-114 | 52.6 | 7.1 | 12.3 | 52.8 | 7.2 | 12.2 |
| 225 | O | double | H | H | 126-127 | 62.7 | 7.2 | 9.1 | 62.7 | 7.4 | 8.9 |
| 231 | O | double | H | C(=O)NHCH₃ | oil | 57.1 | 6.7 | 13.3 | 57.0 | 7.0 | 12.8 |

TABLE IV

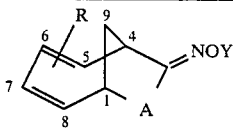

| EX. NO. | A | R | Y | MELTING RANGE °C. | CALCULATED C | H | N | FOUND C | H | N |
|---|---|---|---|---|---|---|---|---|---|---|
| 232 | O | H | H | 141-151 | 63.6 | 6.0 | 9.3 | 63.5 | 6.1 | 9.4 |
| 269 | O | H | C(=O)HNCH₃ | 137-138 | 57.7 | 5.8 | 13.4 | 57.5 | 5.9 | 13.3 |
| 285 | O | 5,6,7,8-(H)₄—5,8-Br₂—6,7-dehydro | C(=O)NHCH₃ | 166-167 | 32.6 | 3.3 | 7.6 | 32.8 | 3.4 | 7.8 |

TABLE V

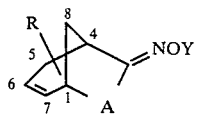

| Ex. NO. | A | R | Y | MELTING RANGE °C. | CALCULATED C | H | N | FOUND C | H | N |
|---|---|---|---|---|---|---|---|---|---|---|
| 283 | S | 6,7-H₂—7-Cl—8-SC₁₂H₂₅—n | C(=O)NHCH₃ | 103-104 | 55.7 | 7.7 | 8.9 | 55.9 | 7.8 | 8.6 |
| 294 | O | 6,7-H₂— | C(=O)NHCH₃ | oily solid | 54.5 | 7.1 | 14.1 | 53.7 | 7.4 | 13.8 |

TABLE VI

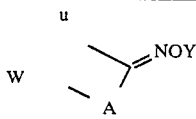

| EX. NO. | A | u | W | Y | MELTING RANGE °C. | CALCULATED C | H | N | FOUND C | H | N |
|---|---|---|---|---|---|---|---|---|---|---|---|
| 146 | S | —OCH₂CH₂— | —HC=C(Cl)— | C(=O)NHCH₃ | 140-142 | 41.2 | 4.2 | 10.7 | 41.6 | 4.4 | 10.4 |
| 174 | S | 1,2-C₆H₄ | 1,2-C₆H₄ | C(=O)NHCH₃ | 172.5-174 | 65.8 | 4.5 | 9.0 | 65.5 | 4.5 | 8.9 |
| 175 | S | 1,2-C₆H₄ | 1,2-C₆H₄ | H | 216-218 | 71.1 | 4.4 | 5.5 | 70.8 | 4.1 | 5.6 |

BIOLOGICAL ACTIVITY

The compounds were evaluated for biological activity against the following representative pests: Southern corn rootworm (*Diabrotica undecimpunctata howardi*), Mexican bean beetle (*Epilachna varivestis*), Southern armyworm (*Spodoptera eridania*), housefly (*Musca domestica*), bean aphid (*Aphis fabae*) and red spider mite (*Tetranychus urticae*). A combination of contact, stomach poison and systemic tests are run on these insects.

The formulation used for insecticide testing contains a final concentration of 0.0128 percent or 128 p.p.m. test chemical, 4 percent acetone and 0.01 percent (100 p.p.m.) Triton X-155 surfactant. Accompanying reference insecticides, if any, are formulated by these procedures as are the checks which contain a standard amount of solvent and a surfactant, but no test chemical. The foregoing stock formulations are utilized with appropriate dilution to obtain the desired pound/acre application rates.

The test procedures employed are as follows.

BEAN APHID SPRAY AND SYSTEMIC TEST

This test determines the insecticidal activity of the compound being tested against the bean aphid, *Aphis fabae*. Stock formulations containing 128 p.p.m. of each test chemical are prepared using 12.8 mg of the test chemical, 4.0 ml acetone containing 0.25 percent (V/V) Triton X-155 and 96.0 ml deionized water and are used in both soil drench and spray treatments. The stock formulations are diluted to obtain the appropriate lower concentrations maintaining the concentration level of all adjuvants. The bean aphid is cultured on nasturtium plants (var. Tall Single), no attempt being made to select insects of a given age in these tests. Single nasturtium test plants growing in soil in individual 3-inch fiber pots are then infested with populations of 100 to 200 aphids.

In the spray applicaton, 50 ml of stock or diluted formulation is uniformly sprayed onto the plants. In the systemic application, 11.2 ml of stock or diluted formulation is applied to the soil containing the plant. A dosage of 11.2 ml of formulation containing 128 p.p.m. of test chemical is equivalent to a dosage of the test chemical of 4 pounds per acre (lb/A).

The plant test units under fluorescent lights are given bottom watering for the duration of the test. Percentage mortality is determined three days after treatment. Results of this test, as expressed in $LC_{50}$ values, are shown in Table VII as A (aphid contact spray) and AS (aphid systemic soil drench).

RED SPIDER MITE SPRAY AND SYSTEMIC TEST

This test determines the acaricidal activity of the compound being tested against the red spider mite, *Tetranychus urticae*. Stock formulations containing 128 p.p.m. of each test chemical are prepared by the procedure above and are used in both the soil drench and spray treatments. The stock culture of mites is maintained on Scarlet runner bean foliage. Approximately 18 to 24 hours before testing, mites are transferred to the primary leaves of a Lima bean plant (var. Sieva) grown in 3-inch pots.

The spray and systemic application methods described before are used to apply the test formulations to the infested plants and soil. After three days, one of the two leaves treated is examined and mortality is determined. Results of this test, as expressed in $LC_{50}$ values, are shown in Table VII as M (mite contact spray test) and MS (mite systemic soil drench test).

HOUSEFLY SPRAY TEST

This test determines the insecticidal activity of the compound being tested against adult houseflies, *Musca domestica*. Stock formulations containing 128 p.p.m. of each test chemical are prepared using the procedure described previously and are diluted to obtain the appropiate lower concentrations.

Ten adult flies are placed in a cylindrical screen cage 1½ by 4 inches fabricated from 20-mesh stainless steel screening and are sprayed with 50 ml of the stock or diluted formulation. The flies are supplied food and drink from a sucrose solution by draping a paper wick over the outside of the screen cylinder and are able to feed and drink ad libitum. Percent mortality obtained is determined three days after treatment. Results of this test, as expressed in $LC_{50}$ values, are shown in Table VII as HF (housefly spray test).

SOUTHERN ARMYWORM LEAF SPRAY TEST

Paired fully expanded primary leaves excised from Scarlet runner bean plants are maintained in plastic tubes containing water and sprayed with the test formulation prepared as described previously. After the spray deposit on the leaves is dry, the paired leaves are separated. One leaf is placed onto 1.5 percent water agar and infested with 10 newly hatched Southern armyworm larvae. The covered test receptacle is held at 72° F. for four days and then the percent mortality is determined. Results of this test, as expressed in $LC_{50}$ values, are shown in Table VII as AW (Southern armyworm spray test).

MEXICAN BEAN BEETLE LEAF SPRAY TEST

This test determines the insecticidal activity of the compound being tested against the Mexican bean beetle, *Epilachna varivestis*. The test procedure is the same as that described for the Southern armyworm with the exception that one-day old larvae of the Mexican bean beetle instead of newly hatched Southern armyworm larvae are used.

These tests are held at 72° F. for four days when mortality and feeding inhibition are determined. The feeding inhibition is an indication of the repellent properties of the test material. Results of this test, as expressed in $LC_{50}$ values, are shown in Table VII as BB (Mexican bean beetle leaf spray test).

TABLE VII

| EXAMPLE NO. | $LC_{50}$ in ppm | | | | | $LD_{50}$ in Kg/hectare | |
|---|---|---|---|---|---|---|---|
| | BB[2] | AW[3] | HF[4] | M[5] | A[6] | MS[7] | AS[8] |
| 13 | 45 | 61 | 35 | 19 | 2.7 | >16 | >16 |
| 14 | 14 | 21 | 37 | 20 | 5.2 | >16 | >16 |
| 20 | 110 | >128 | >128 | >128 | >128 | >16 | >16 |
| 22 | 2.5 | 33 | >128 | >128 | 3.9 | >16 | >16 |
| 23 | 3.0 | 13.5 | 29 | 5.9 | 2.0 | >16 | >16 |
| 24 | 4.7 | 28 | 71 | 6.6 | 3.3 | >16 | >16 |
| 25 | 7.8 | 11 | 50 | >128 | >128 | >16 | 2.9 |
| 26 | 12 | 23 | 32 | 80 | 28 | >16 | >16 |
| 28 | 22 | 11 | 11 | 54 | 2.4 | >16 | >16 |
| 29A | 1.5 | 17 | 105 | 18 | 71 | >16 | >16 |
| 30 | 3.2 | 17 | 5.5 | 100 | 70 | >16 | >16 |
| 31 | 8.2 | 47 | 4.3 | 19 | 4.6 | >16 | >16 |
| 32 | 110 | >128 | 54 | 71 | 16 | >16 | >16 |
| 33 | 5.8 | 32 | 13 | 12 | 1.1 | >16 | 3.9 |
| 36 | 6.0 | 42 | 16 | 4.1 | 1.2 | >16 | >16 |
| 38 | 12 | >128 | 17 | 12 | 20 | >16 | >16 |
| 41 | 2.1 | 30 | 28 | 3.2 | 6.8 | >16 | >8 |
| 43 | 4.6 | 26 | 25 | 38 | 6.3 | >16 | >16 |
| 46 | 11 | >128 | >128 | 90 | 41 | >16 | >16 |
| 49 | 4.1 | 19 | 15 | 2.9 | 0.78 | >16 | >16 |
| 50 | 5.0 | 18 | 45 | 13 | 2.6 | >16 | >16 |
| 52 | 11 | 19 | 36 | 8.0 | 3.2 | >16 | >16 |
| 55 | 33 | >128 | >128 | 114 | 42 | >16 | >16 |
| 56 | 11 | 22 | 40 | 6.9 | 1.5 | >16 | >16 |
| 60 | 5.2 | 34 | 45 | 12 | 3.5 | >16 | >16 |
| 61 | 6.6 | >128 | 32 | 14 | 7.8 | >16 | 12 |
| 65 | 7.2 | 22 | 18 | 6.6 | 1.9 | >16 | >16 |
| 66 | 6.9 | 18 | 32 | 10 | 2.1 | >16 | >16 |
| 68 | 5.0 | 16 | 14 | 7.0 | 10 | >16 | >16 |
| 69 | 11 | >128 | >128 | 32 | >128 | >16 | >16 |
| 70 | 5.8 | 11 | 14 | 59 | 34 | >16 | >16 |
| 71 | 1.6 | 16 | 21 | 35 | 19 | >16 | >16 |
| 72 | 11 | 66 | 14 | 2.7 | 4.4 | >16 | >16 |
| 77 | 1.8 | 21 | 30 | 15 | 7.5 | >16 | >16 |
| 78 | 3.1 | 20 | 17 | 34 | 55 | >16 | >16 |
| 80 | 6.5 | 18 | 25 | 11 | 5.2 | >16 | <16 |
| 82 | 0.39 | 8.2 | 35 | 2.1 | 4.2 | >16 | 13 |
| 83 | 0.83 | 30 | 17 | 5.5 | 3.9 | >6 | >16 |
| 84 | 4.2 | 59 | 12 | 1.2 | 1.5 | >16 | <16 |
| 88 | 0.98 | 6.9 | 97 | 3.6 | 55 | >16 | 13 |
| 89 | 3.7 | 13 | 8.8 | 34 | 30 | >16 | >16 |

TABLE VII-continued

| EXAMPLE NO. | LC$_{50}$ in ppm | | | | | LD$_{50}$ in Kg/hectare | |
|---|---|---|---|---|---|---|---|
| | BB[2] | AW[3] | HF[4] | M[5] | A[6] | MS[7] | AS[8] |
| 90 | 5.2 | 25 | 46 | 15 | 15 | >16 | >16 |
| 91 | 2.2 | 12 | 23 | >128 | 105 | >16 | >16 |
| 93 | 5.2 | 60 | 25 | 2.9 | 1.4 | >16 | 9 |
| 95 | 2.1 | 17 | 29 | 1.2 | 1.6 | 9 | 5.5 |
| 97 | 2.7 | 20 | 12 | 1.2 | 1.0 | 7.5 | 5.6 |
| 98 | 4.7 | 13 | 8.3 | 4.9 | 1.1 | >16 | >16 |
| 99 | 7.4 | 14 | 3.1 | 4.0 | 2.3 | >16 | >16 |
| 100 | 7.7 | 14 | 8.6 | 2.8 | 3.2 | >16 | >16 |
| 101 | 3.3 | 16 | 3.0 | >128 | 22 | >16 | >16 |
| 104 | 5.5 | 45 | 34 | 4.1 | 5.5 | >16 | >16 |
| 105 | 1.7 | 30 | >128 | 4.0 | 9.4 | >16 | >16 |
| 107 | 4.8 | 30 | 27 | 12 | 7.2 | >16 | >16 |
| 108 | 2.3 | 24 | >128 | >128 | >128 | >16 | >16 |
| 109 | 6.2 | 32 | 60 | 14 | 6.9 | >16 | >16 |
| 111 | 7.6 | 25 | 19 | 15 | 7.9 | >16 | >16 |
| 113 | 4.5 | 18 | >128 | 8.0 | >128 | >16 | >16 |
| 114 | 1.9 | 23 | 114 | 4.0 | 87 | >16 | >16 |
| 116 | 2.6 | 11 | >128 | 2.1 | 16 | >16 | >16 |
| 118 | 4.1 | 9.3 | 99 | 4.7 | 2.2 | >16 | >16 |
| 119 | 6.5 | 19 | 131 | 23 | 8.9 | >16 | >16 |
| 120 | 5.3 | 27 | 32 | 18 | 26 | >16 | >16 |
| 121 | 2.6 | 31 | >128 | 4.6 | >128 | >16 | >16 |
| 125 | 8.4 | 24 | 21 | 25 | 22 | >16 | >16 |
| 132 | 4.6 | 19 | 108 | >128 | 11 | >16 | >16 |
| 133 | 2.4 | 14 | 63 | 1.5 | 21 | >16 | >16 |
| 136 | 1.1 | 13 | 88 | 3.6 | 4.2 | 9 | >16 |
| 138 | >128 | >128 | >128 | >128 | >128 | >16 | >16 |
| 142 | 5.2 | 22 | 31 | 19 | 3.0 | >16 | >16 |
| 144 | 49 | >128 | 91 | 8.3 | 105 | >16 | >16 |
| 145 | 1.4 | 18 | 15 | 14 | 2.5 | >16 | 13 |
| 146 | 2.0 | >128 | 22 | 5.0 | 24 | 12 | 14 |
| 148 | 3.3 | 15 | 16 | >128 | 25 | >16 | >16 |
| 149 | 5.3 | 23 | 21 | 18 | 45 | >16 | >16 |
| 150 | 1.2 | 20 | >128 | 2.0 | 139 | <16 | >16 |
| 151 | 2.4 | 24 | 66 | 5.2 | 11 | >16 | >16 |
| 156 | 8.0 | 36 | 100 | >128 | 44 | >16 | >16 |
| 159 | 5.4 | 32 | 47 | 6.0 | 1.6 | >16 | >16 |
| 162 | 5.0 | 16 | 104 | 15 | 12 | >16 | >16 |
| 163 | 7.1 | 17 | 33 | 29 | 11 | >16 | >16 |
| 166 | 7.0 | 25 | 15 | 40 | 49 | >16 | >16 |
| 168 | 4.2 | 34 | 64 | 47 | 56 | >16 | >16 |
| 169 | 3.9 | 22 | 53 | 8.6 | 7.0 | >16 | >16 |
| 171 | 2.1 | 11 | 26 | 4.2 | 59 | >16 | >16 |
| 172 | 16 | 22 | 7.3 | 17 | 8.4 | >16 | 14 |
| 173 | 1.8 | 18 | 23 | 5.7 | 6.1 | >16 | >16 |
| 176 | 1.6 | 17 | 13 | 4.0 | 5.5 | 9 | >16 |
| 179 | 4.2 | 26 | 85 | 13 | 8.9 | >16 | >16 |
| 181 | 14 | 55 | >128 | 16 | 1.4 | >16 | >16 |
| 183 | 14 | 84 | 26 | 7.1 | 4.5 | >16 | <16 |
| 184 | 4.1 | 17 | 48 | 14 | 16 | >16 | >16 |
| 186 | 6.0 | 41 | >128 | 65 | 26 | >16 | >16 |
| 188 | 8.0 | 32 | 26 | 18 | 10 | >16 | >16 |
| 190 | 2.6 | 12 | 125 | 5.7 | 16 | <16 | <16 |
| 196 | 6.1 | 17 | 4.7 | 13 | 1.1 | >16 | <16 |
| 197 | 4.8 | 16 | 87 | 29 | 23 | >16 | <16 |
| 198 | 3.7 | 18 | 4.2 | 6.2 | 1.3 | >16 | >16 |
| 201 | 1.2 | 52 | 87 | 4.9 | 11 | >16 | 2 |
| 210 | 4.2 | 22 | 6.8 | 28 | 2.4 | >16 | 2.1 |
| 211 | 2.6 | 14 | 3.2 | 11 | 0.91 | 9 | 0.2 |
| 238 | 1.9 | 9.0 | 30 | 3.7 | 73 | 16 | 5.5 |
| 240 | 1.7 | 18 | 33 | 36 | 30 | >16 | <16 |
| 246 | 1.2 | 12 | 49 | 7.6 | 12 | >16 | >16 |
| 247 | 2.0 | 17 | >128 | 6.4 | 11 | >16 | >16 |
| 248 | 2.0 | 45 | >128 | 6.1 | 71 | >16 | >16 |
| 261 | 2.7 | 29 | 61 | 3.2 | 15 | >16 | >16 |
| 262 | 1.8 | 23 | 61 | 11 | >128 | >16 | >16 |
| 265 | 2.3 | 31 | 42 | 5.9 | 43 | >16 | >16 |
| 269 | 6.9 | 99 | 26 | 26 | 8.1 | >16 | <16 |
| 271 | 2.0 | 7.6 | 103 | 2.8 | 15 | >16 | <16 |
| 274 | <32 | >128 | 118 | 11 | 16 | <16 | <16 |
| 278 | 3.2 | 28 | 37 | 31 | 42 | >16 | >16 |
| 289 | <32 | 105 | >128 | <32 | 35 | <16 | <16 |
| 290 | 4.2 | >128 | 30 | 6 | 3.7 | <16 | <16 |

[1]LC$_{50}$ = Concentration lethal to 50% of test species
[2]BB = Mexican bean beetle
[3]AW = Southern army worm
[4]HF = housefly
[5]M = mite contact
[6]A = aphid contact
[7]MS = mite systemic
[8]AS = aphid systemic

ROOT-KNOT NEMATODE TEST

This test is an evaluation of the effectiveness of the compounding being tested against infection by root-knot nematodes, *Meloidogyne spp.*

Pasteurized greenhouse soil, diluted by two-thirds with clean washed sand, is infested with about 15 g of nematode infested tomato roots and soil. The test formulation contains 0.056 g of test compound, 4.0 ml stock emulsifier solution (0.25 percent Triton X-155 in acetone by volume) and 96.0 ml deoinized water, giving a concentration of 560 p.p.m. Lower concentrations are achieved by dilution.

Treatment is accomplished by adding 50 ml of the formulated compound into a plastic bag which contains enough infested soil to fill two 4-inch round pots. This is thoroughly mixed, then returned to the pots, after which 5 cucumber seeds (Ohio MR17 var.) are planted per pot.

Two standards are included with each test, Phenamiphos and Aldicarb are most often used, with Carbofuran and Ethoprop used as substitutes. Standard formulations are treated at 140 p.p.m. with lower concentrations achieved by dilution.

Roots are removed from the soil after three weeks of growth and rated for gall (root-knot nematode infection) formation. A rating of infection from 0 to 10 is recorded: 0=no galls or complete control and 10=heavily galled roots comparable to controls. Each of the roots systems is rated separately. The average of each treatment is substracted from the average of the control check, that sum is then divided by the average of the control check and multiplied by 100 to obtain a percent nematode control.

Precent control equals:

$$100 \times \frac{\text{average of control check} - \text{average of treatment}}{\text{average of control check}}$$

The results obtained with selected compounds of the invention are shown in Table VIII.

TABLE VIII

| Compound Example No. | Percent Control At Indicated Rate Dosage (lb/A) | | | | | |
|---|---|---|---|---|---|---|
| | 8 | 4 | 2 | 1 | 0.5 | 0.25 | 0.125 |
| PHENAMIPHOS[1] | 3 | 76 | 57 | 30 | 14 | — | — |
| ALDICARB[2] | — | 78 | 66 | 49 | 14 | — | — |
| 33 | 100 | 99 | 86 | 80 | 76 | 63 | — |
| 34 | — | 95 | — | 74 | — | — | — |
| 36 | 100 | 100 | 100 | 84 | 50 | 24 | — |
| 37 | — | 62 | — | 41 | — | — | — |
| 38 | — | 86 | — | 49 | — | — | — |
| 41 | — | 100 | 97 | 92 | 83 | 70 | 67 |
| 43 | — | 96 | — | 42 | — | — | — |
| 49 | 100 | 100 | 100 | 87 | 67 | 22 | — |
| 50 | 100 | 100 | 100 | 74 | 57 | 5 | — |

TABLE VIII-continued

| Compound Example No. | Percent Control At Indicated Rate Dosage (lb/A) | | | | | | |
|---|---|---|---|---|---|---|---|
| | 8 | 4 | 2 | 1 | 0.5 | 0.25 | 0.125 |
| 52 | 100 | — | 68 | 59 | 31 | 0 | — |
| 58 | — | 100 | — | 85 | 30 | 13 | — |
| 59 | 100 | 79 | 76 | 0 | 14 | — | — |
| 61 | 100 | — | 58 | — | 8 | — | — |
| 67 | — | 100 | — | 90 | — | — | — |
| 68 | — | 99 | — | 72 | — | — | — |
| 70 | — | 85 | — | 48 | — | — | — |
| 71 | — | 98 | — | 74 | — | — | — |
| 72 | — | 100 | — | 73 | — | — | — |
| 77 | — | 66 | — | 25 | — | — | — |
| 79 | — | 100 | — | 78 | — | 20 | — |
| 80 | — | 100 | — | 95 | — | 42 | — |
| 82 | — | 100 | 100 | 95 | 73 | 80 | 69 |
| 83 | — | 100 | — | 90 | — | 51 | — |
| 84 | — | 100 | — | 100 | — | — | — |
| 85 | — | 100 | — | 59 | — | — | — |
| 88 | — | 100 | 83 | 98 | 52 | 64 | 48 |
| 90 | — | 100 | — | 91 | — | — | — |
| 92 | — | 100 | 93 | 93 | 73 | 64 | 49 |
| 95 | — | 99 | — | 100 | — | 87 | — |
| 97 | — | 100 | 94 | 87 | 64 | 50 | 22 |
| 99 | — | 98 | — | 82 | — | 42 | — |
| 100 | — | 97 | — | 78 | — | 19 | — |
| 105 | — | 94 | — | 83 | — | 66 | — |
| 113 | — | 100 | — | 90 | — | 81 | — |
| 114 | — | 100 | — | 84 | — | 57 | — |
| 116 | — | 100 | — | 94 | — | 62 | — |
| 129 | — | 55 | — | 50 | — | 29 | — |
| 130 | — | 22 | — | 29 | — | 38 | — |
| 136 | — | 95 | — | 85 | — | 71 | — |
| 141 | — | 97 | — | 94 | — | 73 | — |
| 142 | — | 74 | — | 54 | — | 14 | — |
| 150 | — | 100 | — | 100 | — | 96 | — |
| 151 | — | 100 | — | 78 | — | 5 | — |
| 165 | — | 100 | — | 91 | — | 47 | — |
| 168 | — | 100 | — | 98 | — | 92 | — |
| 171 | — | 97 | — | 92 | — | 43 | — |
| 176 | — | 99 | — | 89 | — | 63 | — |
| 196 | — | 98 | — | 80 | 65 | — | — |
| 210 | — | 74 | — | 49 | — | 20 | — |
| 227 | — | 100 | — | 75 | — | 39 | — |
| 230 | 100 | 100 | 94 | 84 | — | 0 | — |
| 234 | 100 | 100 | 97 | 67 | — | 0 | — |
| 241 | — | 95 | — | 91 | — | 50 | — |
| 244 | — | 100 | — | 99 | — | 22 | — |
| 246 | — | 100 | — | 100 | — | 100 | 95 |
| 250 | — | 100 | — | 97 | — | 92 | — |
| 261 | — | 100 | — | 99 | — | 96 | 39 |
| 262 | — | 100 | — | 99 | — | 30 | — |
| 264 | — | 100 | — | 100 | — | 69 | — |
| 265 | — | 100 | — | 100 | — | 73 | — |
| 268 | — | 98 | — | 98 | — | 22 | — |
| 269 | — | 64 | — | 48 | — | 68 | — |
| 271 | — | 94 | — | 64 | — | 34 | — |
| 272 | — | 90 | — | 70 | — | 59 | — |
| 274 | — | 70 | — | 44 | — | 22 | — |
| 276 | — | 88 | — | 78 | — | 52 | — |

$^{1,2}$ = Mean of all replications.
$^3$ = Not tested.

SOUTHERN CORN ROOTWORM (LARVAE OF SPOTTED CUCUMBER BEETLE)

The test organisms are six- to ten-day old larvae of a chlorinated hydrocarbon resistant strain of *Diabrotica Undecimpunctata howardi* Barb. On the day before test compounds are to be screened, to one ounce polystyrene cups (one cup per test compound) are added: one level teaspoon (5 cm$^3$) air dried greenhouse soil, five corn seeds (Zea mays L. var. Popcorn) treated with thiram and a second teaspoon of dry soil. The following day, 0.45 ml of standard 128 p.p.m. formulation and 2.0 ml of water are added and the cups are capped.

The sample cups are stored under conditions of high humidity in a room at 72°–78° F. After four days, the corn seedlings will have shoots 0.5 to 1 inch long, and they will have heaved the covering soil. At this time, 5 to 10 larvae are dropped into each test unit. The cups are then returned to the holding room. Three days after infestation, the test is read. Precentage mortality is determined at the dosage rate. The results are summarized in Table IX.

TABLE IX

| Compound Example No. | Rate (PPM) | Corn Rootworm (Percent Mortality) |
|---|---|---|
| 82 | 128 | 100 |
| 113 | 128 | 100 |
| | 64 | 100 |
| | 32 | 20 |
| 170 | 128 | 33 |
| | 64 | 46 |
| 172 | 128 | 55 |
| | | 9 |

In addition to the foregoing evaluation, certain of the thiolhydroximidate compounds of the invention were subjected to the following special tests to determine the presence of other significant biological properties for these compounds.

PLANT GROWTH REGULANT ACTIVITY

Compounds of the invention were evaluated relative to plant growth regulant activity against three plant species in a petri dish test. The test is divided into a primary test where 500 μg and 100 μg chemical per petri dish (100 ×25 mm, disposable) are tested simultaneously and a secondary test where 50 μg, 10 μg and 1 μg chemical per petri dish are tested simultaneously. Compounds which pass the primary test are further evaluated in the secondary test. A special petri dish test may also be run to evaluate particular test compounds, in which case all five rates, i.e., 500, 100, 50, 10 and 1 μg per petri dish, are tested simultaneously.

According to the test procedure, three plant species are planted in a petri dish which has been treated with the test substance. The three species are as follows: (1) a mixture of approximately 50 percent light-sensitive and 50 percent light-insensitive lettuce (*Lactuca sativa* L. 'Grand Rapids'); (2) soft red winter wheat [*Triticum aestivum* L. (Aestivicum Group) 'Abe']; and (3) pasture-type perennial ryegrass (*Lolium perenne* L. 'Linn'). Wheat and perennial ryegrass seeds are surface-sterilized with 1 percent sodium hpochloride for 10 minutes and 5 minutes, respectively.

Each test compound is formulated in acetone and aliquots of the test formulation are placed on three layers of sterilized filter papers (Whatman No. 1, 8.26 cm diameter) in each petri dish. As seen as the acetone evaporates, 7 ml of deionized water are added into each petri dish with an appropriate automatic dispenser. Then, 5 to 8 wheat seeds, 10 to 15 perennial ryegrass seeds and 10 to 15 lettuce seeds are placed on the filter paper of each petri dish. Dishes are then covered and seeds are germinated for 3 days at 20° C. at a relative humidity of 65 in the dark. The dishes are then removed from the dark growth chamber and maintained in lighted environmental growth chambers for 4 days.

At the end of the seventh day of planting, growth and developmental responses/characteristics are evaluated.

The compounds of Example Nos. 1, 2, 11, 12, 44, 45, 48, 54, 63, 64, 73, 76, 94 and 134 exhibited growth retardant activity. Seed germination, root length and hypocotyl length of lettuce were inhibited (i.e., between 15 percent and 85 percent inhibition compared to untreated controls) at rates ranging from about 100 μg/dish to 2000 μg/dish. Root and coleoptile growth of wheat and ryegrass was inhibited at rates ranging from 10 μg/dish to 2000 μg/dish.

Growth stimulation activity was observed with growth of lettuce treated with these compounds was stimulated at rates ranging from about 50 μg/dish to 500 μg/dish.

ANTIFUNGAL ACTIVITY

Preselected thiolhydroximates of the invention were incorporated into an agar based fungal growth medium. Spore suspensions of five different fungus species were prepared. Drops of each suspension were incubated for 24 or 48 hours. The spores were observed microscopically and rated as indicated in Table X.

TABLE X

| Compound Ex. No. (1000 ppm) | Alternaria solani 24° C. 24 hr | Helminthosporium oryzae 24° C. 24 hr | Botrytis cinerea 20° C. 24 hr | Colletotrichum lagenarium 20° C. 48 hr | Colletotrichum trifoliorum 20° C. 48 hr |
|---|---|---|---|---|---|
| 11 | 2 | 1 | 1 | 0 | 0 |
| 64 | 2 | 4 | 0 | 0 | 0 |
| 73 | 1 | 0 | 0 | 0 | 0 |
| 76 | 0 | 0 | 0 | 0 | 0 |

KEY
0 — no germination, no growth
1 — germination, no growth
2 — some growth
3 — ~50% inhibition
4 — slight inhibition While the invention has been described and illustrated with reference to certain preferred embodiments thereof, those skilled in the art will appreciate that various changes, modifications and substitutions can be made therein without departing from the spirit of the invention. For instance, dosage rates other than the prefered ranges set forth hereinabove may be applicable as a consequence of variations in soils with respect to permeability, natural plant productivity, prior chemical treatment, etc., as well as difference in environmental conditions, including light, moisture, temperature, wind and the like. Likewise, the specific results observed with respect to pest control may vary depending on whether the active compounds of the present invention are used along or in combination with each other or other known agents as well as the specific type of formulaton employed in applying same to the pests as their habitat and such expected variations in results are contemplated in accordance with the objects and practices of the present invention. It is intended, therefore, that the invention be limited only by the scope of the claims which follow.

What is claimed is:

1. A heterobicyclic compound of the formula:

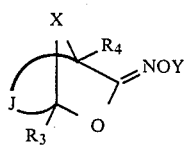

(III)

wherein
J represents the group

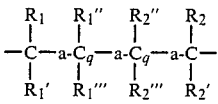

where q, independently, is 0 or 1, a, independently, is a single or double bond and $R_1$, $R_1'$, $R_1''$, $R_1'''$, $R_2$, $R_2'$, $R_2''$ and $R_2'''$ are defined below;

X represents a bridge member selected from

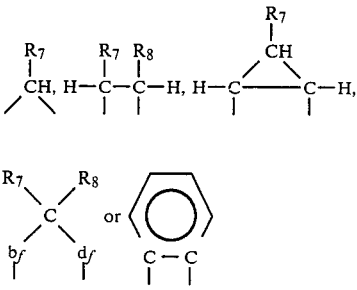

where $R_7$ and $R_8$ independently represent hydrogen, halogen, cyano, lower alkyl, lower alkoxy, lower alkoxycarbonyl or lower alkylthio;

$R_1$–$R_1'''$, inclusive, $R_2$–$R_2'''$, inclusive, $R_3$ and $R_4$ independently represent hydrogen, halogen, hydroxy, cyano, lower alkyl, lower alkoxy, lower haloalkyl, lower alkylcarboxy, arylcarboxy, lower alkylaminocarboxy, carbamoyl, lower alkylcarbamoyl, lower dialkylcarbamoyl, lower alkylthio, lower alkylsulfinyl, lower alkylsulfonyl, lower alkyl ($NH_2$), lower dialkyl ($NH_2$), lower alkoxycarbonyl, trifluoromethyl, pyrrolidyl, phenyl, nitro, thiocyano, thiocarbamyl, lower alkylthiocarbamyl, lower dialkylthiocarbamyl, arylthiocarbamyl or the group

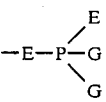

where E is O or S and G represents lower alkyl, lower alkoxy, lower alkylthio, $NH_2$, lower alkyl ($NH_2$) or lower dialkyl($NH_2$);

g is 0, 1 or 2;

Y represents hydrogen or

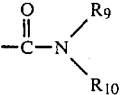

(1)

wherein $R_9$–$R_{10}$ independently represent hydrogen, lower alky, hydroxy lower alkyl, lower alkenyl, lower alkynyl, lower aralkyl, lower alkoxyalkyl or lower polyoxyalkylene; or

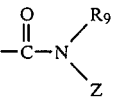

(2)

where $R_9$ is the same as defined before and Z represents

 (a)

where n is 0, 1 or 2 and $R_{11}$ is pyridyl, pyrimidyl, phenyl or phenyl substituted with at least one member selected from hydroxy, lower alkyl, lower alkoxy, halogen, nitro, trifluoromethyl or cyano;

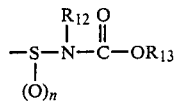 (b)

where n is 0, 1 or 2, and $R_{12}$ is lower alkyl, lower alkoxyalkyl or

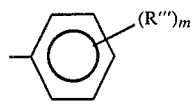

where m is 0, 1, 2 or 3 and R''' is hydrogen, halogen, cyano, nitro, lower alkyl, lower alkoxy, lower alkythio, lower alkylsulfonyl or phenyloxy and $R_{13}$ is lower alkyl, lower alkoxyalkyl, naphthyl, lower alkylthioalkyl

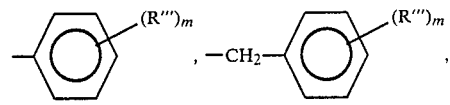

where $(R''')_m$ is as define before,

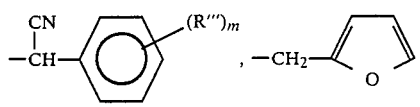

or Q where Q-OY represents formula (III) as defined herein;

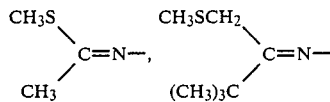 (c)

where $R_{12}$–$R_{13}$ are as defined before;

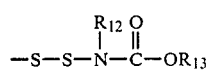 (d)

where n is 0, 1 or 2, $R_{14}$ is phenyl, lower alkyl, lower alkoxyalkyl, lower alkanoyl, lower alkoxycarbonylalkyl, lower alkylthioalkyl, lower carboxyalkyl and $R_{15}$ is lower alkyl,

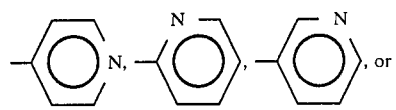

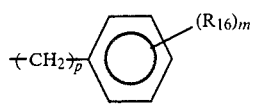

where m is 0–5, p is 0–5 and $R_{16}$ is halogen, lower alkyl, trifluoromethyl, nitro or lower alkoxy;

(e) —S-N$R_{17}R_{18}$ where $R_{17}$–$R_{18}$ are lower alkyl, aryl or together with the nitrogen atom represent

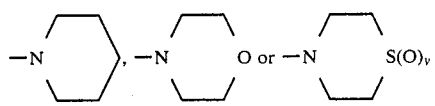

where v is 0, 1 or 2 or

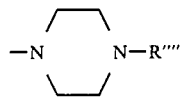

where R'''' is lower alkyl;

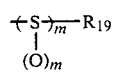 (f)

where n is 0, 1 or 2, m is 1 or 2 and $R_{19}$ is lower alkyl, lower cycloalky, lower haloalkyl, lower cyanoalkyl, lower alkoxycarbonyl, lower (alkylthio)carbonyl, lower alkoxy(thiocarbonyl), lower alkylthio(thiocarbonyl), aryl or substituted aryl with at least one substituent selected from halogen, cyano, nitro, lower alkyl, lower alkoxy, lower alkylthio, lower alkylsulfonyl or phenyloxy, with the proviso that when $R_{19}$ is aryl or substituted aryl, m is 2;

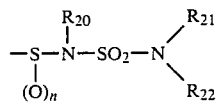 (g)

where n is 0, 1 or 2, $R_{20}$ is lower alkyl and $R_{21}$–$R_{22}$ are the same as $R_{17}$–$R_{18}$ as defined before;

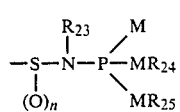 (h)

where n is 0, 1 or 2, M, independently, is S or O and $R_{23}$–$R_{25}$ independently represent lower alkyl or $R_{24}$ and $R_{25}$ together represent

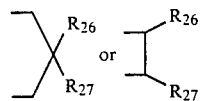

where $R_{26}$–$R_{27}$ independently represent hydrogen or lower alkyl;

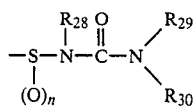 (i)

where n is 0, 1 or 2, $R_{28}$ is lower alkyl or aryl and $R_{29}$–$R_{30}$ independently represent hydrogen, lower alkyl, aryl or lower alkoxy;

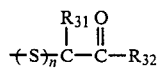 (j)

where n is 1 or 2, $R_{31}$ is lower alkyl and $R_{32}$ is fluoro, lower alkyl, aryl or lower aralkyl;

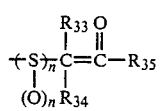 (k)

where m is 0, 1 or 2, n is 1 or 2 and $R_{33}$–$R_{35}$ independently represent hydrogen or lower alkyl;

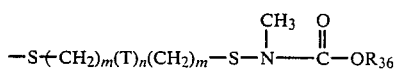 (l)

where T is O, S or —CH$_2$—, m is 1 or 2, n is 0 or 1 and $R_{36}$=$R_{13}$ as defined before;

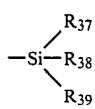 (m)

where $R_{37}$–$R_{39}$ are lower alkyl or aryl;

 (n)

where L represents lower alkyl, cyano, lower alkoxy, aryloxy, lower alkylthio, arylthio or —ON=CR$_{40}$R$_{41}$ where $R_{40}$–$R_{41}$ are the same as $R_{12}$–$R_{13}$ as defined before; or

 (o)

where V represents halogen, lower alkoxy or lower alkylthio;
and further provided the term "aryl" or terms incorporating the root word "aryl" as used throughout this claim means phenyl or naphthyl.

2. The compound of claim 1 wherein the compound is selected from

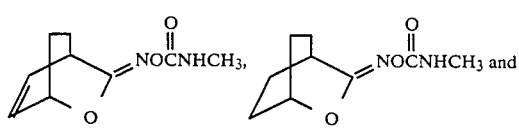

-continued

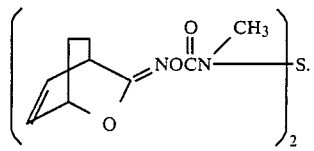

3. An insecticidal and nematocidal composition consisting essentially of a carrier and an insecticidally and nematocidally effective amount of a heterobicyclic compound of the formula:

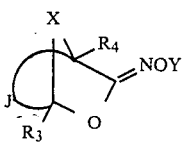 (III)

wherein
J represents the group

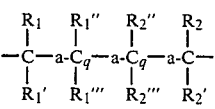

where q, independently, is 0 or 1, a , independently, is a single or double bond and $R_1$, $R_1'$, $R_1''$, $R_1'''$, $R_2$, $R_2'$, $R_2''$ and $R_2'''$ are defined below;
X represents a bridge member selected from

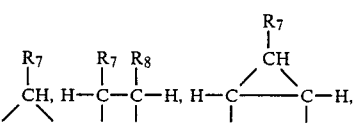

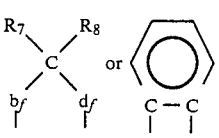

where $R_7$ and $R_8$ independently represent hydrogen, halogen, cyano, lower alkyl, lower alkoxy, lower alkoxycarbonyl or lower alkylthio;
$R_1$–$R_1'''$, inclusive, $R_2$–$R_2'''$, inclusive, $R_3$ and $R_4$ independently represent hydrogen, halogen, hydroxy, cyano, lower alkyl, lower alkoxy, lower haloalky, lower alkylcarboxy, arylcarboxy, lower alkylaminocarboxy, carbamoyl, lower alkylcarbamoyl, lower dialkylcarbamoyl, lower alkylthio, lower alkylsulfinyl, lower alkylsulfonyl, lower alkyl(NH$_2$), lower dialkyl(NH$_2$), lower alkoxycarbonyl, trifluoromethyl, pyrrolidyl, phenyl, nitro, thiocyano, thiocarbamyl, lower alkylthiocarbamyl, lower dialkylthiocarbamyl, arylthiocarbamyl or the group

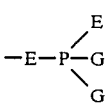

where E is O or S and G represents lower alkyl, lower alkoxy, lower alkylthio, NH₂, lower alkyl(NH₂) or lower dialkyl(NH₂);

g is 0, 1 or 2;

Y represents hydrogen or

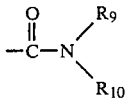 (1)

wherein R₉–R₁₀ independently represent hydrogen, lower alkyl, hydroxy lower alkyl, lower alkenyl, lower alkynyl, lower aralkyl, lower alkoxyalkyl or lower polyoxyalkylene; or

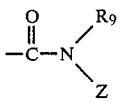 (2)

where R₉ is the same as defined before and Z represents

 (a)

where n is 0, 1 or 2 and R₁₁ is pyridyl, pyrimidyl, phenyl or phenyl substituted with at least one member selected from hydroxy, lower alkyl, lower alkoxy, halogen, nitro, trifluoromethyl or cyano;

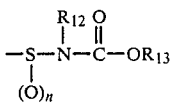 (b)

where n is 0, 1 or 2, and R₁₂ is lower alkyl, lower alkoxyalkyl or

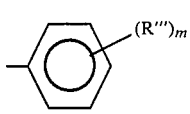

where m is 0, 1, 2 or 3 and R''' is hydrogen, halogen, cyano, nitro, lower alkyl, lower alkoxy, lower alkylthio, lower alkylsulfonyl or phenyloxy and R₁₃ is lower alkyl, lower, alkoxyalkyl, naphthyl, lower alkylthioalkyl

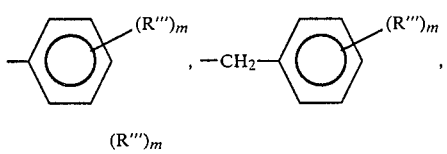

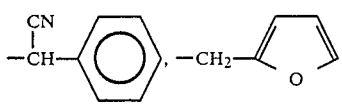

where (R''')ₘ is as defined before,

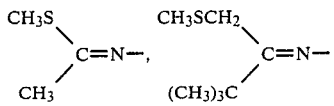

or Q where Q-OY represents formula (III) as defined herein;

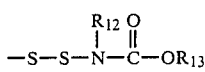 (c)

where R₁₂–R₁₃ are as defined before;

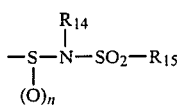 (d)

where n is 0, 1 or 2, R₁₄ is phenyl, lower alkyl, lower alkoxyalkyl, lower alkanoyl, lower alkoxycarbonylalkyl, lower alkylthioalkyl, lower carboxyalkyl and R₁₅ is lower alkyl,

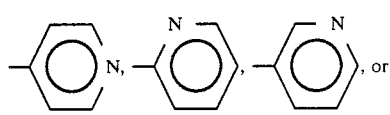

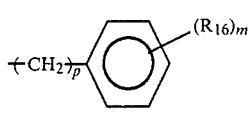

where m is 0–5, p is 0–5 and R₁₆ is halogen, lower alkyl, trifluoromethyl, nitro or lower alkoxy;

(e) —S-NR₁₇R₁₈ where R₁₇–R₁₈ are lower alkyl, aryl or together with the nitrogen atom represent

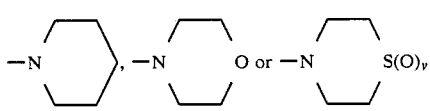

where v is 0, 1 or 2 or

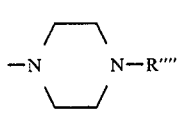

where R'''' is lower alkyl;

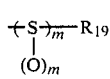 (f)

where n is 0, 1 or 2, m is 1 or 2 and R₁₉ is lower alkyl, lower cycloalkyl, lower haloalkyl, lower cyanoalkyl, lower alkoxycarbonyl, lower (alkylthio)-carbonyl, lower alkoxy(thiocarbonyl), lower alkylthio(-thiocarbonyl), aryl or substituted aryl with at least one substituent selected from halogen, cyano, nitro, lower alkyl, lower alkoxy, lower alkylthio, lower alkylsulfonyl or phenyloxy, with the proviso that when $R_{19}$ is aryl or substituted aryl, m is 2;

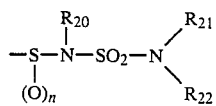 (g)

where n is 0, 1 or 2, $R_{20}$ is lower alkyl and $R_{21}$-$R_{22}$ are the same as $R_{17}$-$R_{18}$ as defined before;

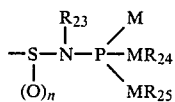 (h)

where n is 0, 1 or 2, M, independently, is S or O and $R_{23}$-$R_{25}$ independently represent lower alkyl or $R_{24}$ and $R_{25}$ together represent

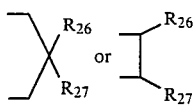

where $R_{26}$-$R_{27}$ independently represent hydrogen or lower alkyl;

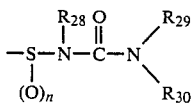 (i)

where n is 0, 1 or 2, $R_{28}$ is lower alkyl or aryl and $R_{29}$-$R_{30}$ independently represent hydrogen, lower alkyl, aryl or lower alkoxy;

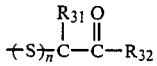 (j)

where n is 1 or 2, $R_{31}$ is lower alkyl and $R_{32}$ is fluoro, lower alkyl, aryl or lower aralkyl;

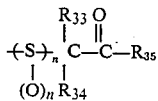 (k)

where m is 0, 1 or 2, n is 1 or 2 and $R_{33}$-$R_{35}$ independently represent hydrogen or lower alkyl;

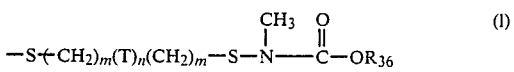 (l)

where T is O, S or —$CH_2$—, m is 1 or 2, n is 0 or 1 and $R_{36}$=$R_{13}$ as defined before;

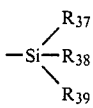 (m)

where $R_{37}$-$R_{39}$ are lower alkyl or aryl;

 (n)

where L represents lower alkyl, cyano, lower alkoxy, aryloxy, lower alkylthio, arylthio or —ON=$CR_{40}R_{41}$ where $R_{40}$-$R_{41}$ are the same as $R_{12}$-$R_{13}$ as defined before; or

 (o)

where V represents halogen, lower alkoxy or lower alkylthio;

and further provided the term "aryl" or terms incorporating the root word "aryl" as used throughout this claim means phenyl or naphthyl.

4. An insecticidal and nematocidal method which consists essentially of applying to the insects or nematodes, or a habitat thereof an insecticidally or nematocidally effective amount of the composition as defined in claim 3.

* * * * *